United States Patent [19]

Swearingen et al.

[11] 4,263,918

[45] Apr. 28, 1981

[54] METHODS OF AND APPARATUS FOR THE MEASUREMENT OF BLOOD PRESSURE

[75] Inventors: Jerry D. Swearingen; Robert C. Watson, both of Gainesville, Fla.

[73] Assignee: Biomega Corporation, Gainesville, Fla.

[21] Appl. No.: 779,374

[22] Filed: Mar. 21, 1977

[51] Int. Cl.³ .............................................. A61B 5/02
[52] U.S. Cl. ...................................................... 128/681
[58] Field of Search ................... 128/2.05 A, 2.05 M, 128/2.05 Q, 2.05 T, 680–681; 364/417

[56] References Cited

U.S. PATENT DOCUMENTS

| | | | |
|---|---|---|---|
| 3,229,685 | 1/1966 | Ringkamp et al. | 128/2.05 A |
| 3,482,565 | 12/1969 | Gowen | 128/2.05 A |
| 3,552,383 | 1/1971 | Krueger | 128/2.05 A |
| 3,581,734 | 6/1971 | Croslin | 128/2.05 M |
| 3,655,095 | 4/1972 | Kienitz | 128/214 E |
| 3,779,235 | 12/1973 | Murphy, Jr. et al. | 128/2.05 M |
| 3,903,872 | 9/1975 | Link | 128/2.05 M X |
| 3,978,848 | 9/1976 | Yen et al. | 128/2.05 T X |
| 3,985,123 | 10/1976 | Herzfinger et al. | 128/2.05 T X |
| 4,009,709 | 3/1977 | Link et al. | 128/2.05 M X |
| 4,033,336 | 7/1977 | Murawski et al. | 128/2.05 A X |
| 4,050,452 | 9/1977 | Lee | 128/2.05 A |
| 4,058,118 | 11/1977 | Stupay et al. | 128/2.05 T |
| 4,074,711 | 2/1978 | Link et al. | 128/2.05 M X |
| 4,154,238 | 5/1979 | Link | 128/681 |
| 4,174,707 | 11/1979 | Link et al. | 128/681 |

OTHER PUBLICATIONS

"Up Checks EKG and Pressure", Electronics Design, v. 2A, #19, p. 28, Sep. 1976.
Schulze, A. E. et al., "A System for Automatic Measurement and Digital Display of Systolic and Diastolic Blood Pressures", Southwest IEEE Proc. Conf. Rec., Apr. 1968, pp. 17F1–17F5.
Link, W. T., "Norse Systems Automatic BP Monitor Using Waveform Analysis Oscillometry", NSI Inc., 3475 Investment Blvd., Hayward, Cal. 94545, Aug. 1974.
Hartley, R. W., "Analogue Display Rate Meter Built Around Digital Switching Elements", MB Engr., Jan. 1976, pp. 107–108.
Randall, J. R. et al., "Computer Automation of BP Measurements", Proceedings of the IEEE, vol. 63, No. 10, 10/75, pp. 1399–1403.

Primary Examiner—Robert W. Michell
Assistant Examiner—Francis J. Jaworski
Attorney, Agent, or Firm—Martin LuKacher

[57] ABSTRACT

Blood pressure is measured with the aid of a programmed data processor such as a microcomputer. Electrical signals are provided in response to the pressure in a blood pressure cuff as the pressure therein is changed to vary the constriction of an artery. The signals are processed to provide a train of pulses corresponding to successive blood pressure pulses and digital signals representing the amplitude of each pulse and the cuff pressure which accompanies each pulse are stored in the memories of the data processor. The processor has means by which the pulses are first selected in accordance with their relative amplitudes and location in the train so as to satisfy criteria for the rejection of artifacts. The processor provides outputs from its memories in which digital signals representing cuff pressures which were acquired at the same time as the pulses which are identified as occurring at the times of the systolic and diastolic events. These outputs may be displayed as on a digital readout device or processed for remote transmission so as to indicate the blood pressure. Information as to the pulse rate may be obtained from the time intervals between a group of pulses in the train by converting that time interval into a digital signal which represents the pulse rate. This signal may also be outputted to a display or for remote transmission.

65 Claims, 17 Drawing Figures

METHODS OF AND APPARATUS FOR THE MEASUREMENT OF BLOOD PRESSURE

The present invention relates to sphygmomanometry and particularly to methods of and apparatus for the measurement of blood pressure.

The invention is especially suitable for providing an electronic instrument whereby blood pressures, upon the occurrence of the systolic and diastolic events, are measured and displayed for observation; the pressure which is measured being the pressure in a compression cuff which is wrapped around the limb or extremity of the body, which cuff pressure is indirectly related to blood pressure. The invention is also applicable to the direct measurement of blood pressure where the blood itself or a membrane presents the blood pressure directly to the instrument. The invention may also be applied to other measurements of parameters representing operations of the circulatory system, such as the measurement of the compliance of arterial walls. Applications for the invention may be found wherever pulses corresponding to the palpitations due to the pumping action of the heart are directly or indirectly available for conversion into corresponding electrical signals, as by means of microphones or other sensing devices.

The measurement of blood pressure has been recognized as a diagnostic tool for upwards of 100 years. The most common way of measuring blood pressure is through the use of a compression bag which is in the form of a cuff for the application of external pressure to an artery. The cuff pressure is read by a manometer which is calibrated in terms of millimeters of mercury. The pressure in the cuff is raised above the point at which the artery is occluded and allowed to slowly decrease. The pressure at which the blood first begins to flow through the partially occluded artery is considered to be the systolic pressure. The diastolic pressure is usually determined by an auscultatory technique of listening to the so called "Korotkoff" sounds in the artery distal to the cuff by means of a stethoscope. An experienced observer is required to determine the systolic and diastolic pressure events accurately. Accordingly, blood pressure measurement by the conventional sphygmomanometer is subject to human measurement errors such as: bias from past medical records; poor hearing; poor operator technique; distraction—forgetting results; improper operator training; missing an auscultatory gap; confusion by artifacts as may be due to biqniny, arrhythmias, and other cardiovascular irregularities; misinterpretation of the diastolic pressures, particularly for those cases where the fourth and fifth phases of the Korotkoff sounds are indistinct; and misinterpretation of the presence or absence of heart beat in cases where the heart beats are weak. The need to eliminate these human measurement errors, as well as the need to increase the speed and decrease the difficulty of blood pressure measurement has resulted in a continuing search for new and improved methods for the automatic non-invasive measurement of blood pressure, particularly by electronic means.

A survey of efforts in this search was published by the National Aeronautics and Space Administration in a document entitled "The Measurement of Blood Pressure in the Human Body—a state-of-the-art summary oriented to non-medical scientists and engineers", by C. R. Smith and W. H. Bickley, NASA SP-5006, dated April, 1964. Another such survey appears in L. A. Geddes, "The Direct and Indirect Measurement of Blood Pressure", Year Book Medical Publishers, Chicago, Ill. (1970). Of the known kinds of automatic and semi-automatic electronic blood pressure measuring instruments, many are based upon auscultatory methods for the detection and analysis of the Korotkoff sounds. Others are based on the so-called oscillometric method of analyzing signals related to the blood pressure waveform. Still others seek to measure blood pressure in terms of the impedance presented by the artery, either directly or by Doppler techniques. Still others analyze the variations in the volume or flow of the blood as into and out of an extremity (e.g., a finger) and may be referred to as being based upon volumetric techniques. Various transducers and cuff pressure control arrangements have been suggested in an attempt to improve upon these instruments.

For further information respecting instruments based upon Korotkoff sounds or auscultatory techniques, reference may be had to the following U.S. Patents: Smith, No. 3,157,177 issued Nov. 17, 1964; Vick, No. 3,467,837 issued Sept. 16, 1969; Kahn et al, No. 3,508,537 issued Apr. 28, 1970; Hobel, No. 3,633,568 issued Jan. 11, 1972; Egli et al, No. 3,651,798 issued Mar. 28, 1972; Sanctuary, No. 3,654,915 issued Apr. 11, 1972; Fernandez, No. 3,744,490 issued July 10, 1973; Hurwitz, No. 3,771,515 issued Nov. 13, 1973; Fletcher et al, No. 3,814,083 issued June 4, 1974; Sanderson No. 3,878,834 issued Apr. 22, 1975; Lichowsky, No. 3,905,354 issued Sept. 16, 1975; Maurer et al, No. 3,930,494 issued Jan. 6, 1976.

Instruments utilizing the volumetric technique are discussed in the following U.S. Patents: Boucke et al, No. 2,875,750 issued Mar. 3, 1959; Halpern, No. 3,104,661 issued Sept. 24, 1963; Green, No. 3,143,111 issued Aug. 4, 1964; Bolie, No. 3,149,628 issued Sept. 22, 1964; Nakayama, No. 3,920,004 issued Nov. 18, 1975.

Reference may be had to the following U.S. Patents for further information respecting instruments using Doppler or impedance measurement techniques: Tolles, No. 3,095,872 issued July 2, 1963; King et al, No. 3,605,723 issued Sept. 20, 1971; Massie, No. 3,885,551 issued May 27, 1975.

Instruments based upon the analysis of the blood pressure waveform (viz. the oscillometric technique) are discussed in the following U.S. Patents: Funfstuck, No. 3,400,709 issued Sept. 10, 1968; Eklof, No. 3,658,060 issued Apr. 25, 1972; Day et al, No. 3,714,939 issued Feb. 6, 1973; Traite, No. 3,224,435 issued Dec. 21, 1965; Gebben at al, No. 3,850,169 issued Nov. 26, 1974; Birnbaum, No. 3,893,452 issued July 8, 1975; Link, No. 3,903,872 issued Sept. 9, 1975; Birnbaum et al, No. 3,938,506 issued Feb. 17, 1976.

Reference may also be had to the above-mentioned NASA publication and Geddes text for further information respecting other instruments based on the oscillometric technique as well as the other techniques discussed above.

Various transducer designs for non-invasive detection of blood pressure indicating signals are shown in Pressman et al, U.S. Pat. No. 3,219,035 issued Nov. 23, 1965; Blick, U.S. Pat. No. 3,880,145 issued Apr. 29, 1975; and Cannon et al, U.S. Pat. No. 3,894,535 issued July 15, 1975. An arrangement for controlling the pressure and volume of fluid applied to a blood pressure cuff is shown in Lem et al, U.S. Pat. No. 3,527,204 issued Sept. 8, 1970; and in Lichowsky, U.S. Pat. No. 3,905,353 issued Sept. 16, 1975.

Notwithstanding the recognition of the need for method and apparatus which would be capable of automatically or semiautomatically measuring blood pressure and the efforst which have heretofore been exerted in attempts to fulfill that need, a reliable and effective method, which can be implemented in an instrument of reasonable cost, has not heretofore been discovered. Of the instruments which are available, almost all are based upon the auscultatory technique wherein the Korotkoff sounds or arterial wall movements are sensed by microphones or ultrasonic transducers, and in some cases by a human listening to a stethoscope. These are subject to additional errors if the microphone or other transducer for sensing of the sounds is not carefully positioned over the artery being occluded. Only one instrument is available which is based upon oscillometric waveform analysis techniques of the sort discussed in U.S. Pat. No. 3,903,872 which is mentioned above. A few instruments are based upon Doppler techniques of the sort discussed in U.S. Pat. No. 3,605,723 which is also mentioned above.

Another difficulty and problem which militates against the accuracy of blood pressure measurement is the presence of artifacts. Such artifacts may be due to cardiovascular irregularities and even to the inadvertent bumping of the blood pressure cuff or the movement of the patient while the blood pressure is being measured, which of course is difficult to avoid when taking measurements on children or animals.

It is a principal object of the present invention to provide improved methods of and apparatus for sphygmomanometry whereby blood pressure and other information respecting the operation of the circulatory system may be obtained.

It is another object of the present invention to provide improved methods of and apparatus for the measurement of blood pressure.

It is a further object of the present invention to provide methods of and apparatus for the measurement of blood pressure which methods and apparatus are also adapted to measure pulse rate.

It is a still further object of the present invention to provide improved methods of and apparatus for the measurement of blood pressure which obtains information as to the systolic and diastolic pressures by the analysis of the blood pressure waveform or oscillometric pulse train.

It is a still further object of the present invention to provide improved methods of and apparatus for the measurement of blood pressure which are operative to prevent erroneous measurement due to artifacts.

It is a still further object of the present invention to provide improved methods of and apparatus for the automated measurement of blood pressure which has measurement accuracy comparable to the accuracy of conventional auscultatory methods carried out by trained personnel who use a stethoscope, blood pressure cuff and manometer arrangement manually to measure blood pressure.

It is a still further object of the present invention to provide improved methods of and apparatus for measurement of blood pressure which may be used for adults and children and even for animals.

It is a still further object of the present invention to provide an improved instrument for the automated measurement of blood pressure which is operative to acquire and analyze inputs obtained during a measurement with the aid of a programmed data processor, which may be a microcomputer.

It is a still further object of the present invention to provide an improved instrument for measuring blood pressure which is also adapted to check pulse rate which may be implemented in a package which is small in size and portable and which is easy to operate and use for attaining accurate measurements even where untrained personnel operate the instrument or the instrument is operated by a patient to take his or her own blood pressure and/or pulse rate.

It is still a further object of the present invention to provide improved methods of and instrumentation for the measurement of blood pressure which is operative to display an error or alarm signal where incorrect results may be obtained due to improper operation or the presence of artifacts which would cause erroneous results.

It is a still further object of the present invention to provide improved methods of and instrumentation for periodic or programmed monitoring of blood pressure (say over a long term) with an automatic cuff inflating and deflating system.

Briefly described, the invention makes use of the steady state or static pressure as is applied to constrict or occlude a blood vessel and the pulsatile component of that pressure which is in the form of an oscillometric pulse train with each pulse corresponding to a successive pulsation of the heart. It has been discovered in accordance with the invention that a certain proportionality exists between the amplitude of the pulse where the systolic event occurs and a reference based upon the peak value of a set of pulses in the train. There is also a proportionality between this reference and the amplitude of the pulse in the train where the diastolic event occurs. The pulse train accompanies the constriction of the vessel and can be obtained either on the inflation cycle (viz, toward greater constriction and higher cuff pressures) or on the deflation cycle (while the constriction of the vessel is decreased and toward lower cuff pressures). This may be thought of as either on the up ramp (toward higher cuff pressures) or the down ramp (toward lower cuff pressures) of the cycle. The systolic event corresponds to a pulse on the side of the pulses in the set forming the reference toward higher cuff pressures, while the diastolic event is found on the side of the pulse set toward lower cuff pressures. The detection of artifacts and incorrect operation is based upon the determination of the amplitude relationships between various pulses in the train and the location of certain pulses in the train.

More specifically, signals as to the static pressure in the cuff and the pulse train which is caused by the heart pumping action on the cuff, are obtained as by means of a pressure transducer coupled to the cuff and a bandpass filter which transmits the pulsatile components of the pulse train. Data is stored as to the amplitudes of each pulse and the cuff pressure corresponding thereo. The cuff pressure may be considered to follow the envelope of the pulse train. This data may be in the form of digital signals which are arranged in three tables: namely, a table of digital signals corresponding to a plurality of the highest pulses in the train which may be called the peak table; a table corresponding to the pulses in the train, which may be called the pulse table, and a table corresponding to the cuff pressures for each of the pulses which may be called the cuff table. The reference is obtained from the peak table. In order to detect and reject artifacts, the pulses in the peak table are sorted and additional pulses acquired and inserted into the peak table as the measurement proceeds, until the amplitude relationships are satisfied, or the supply of pulses is exhausted (viz, the cuff pressure dropped below a point where accurate measurements are obtainable at the end of a constriction cycle).

It has been found in accordance with the invention that artifacts are rejected when the highest peak in a set of three adjacent pulses in the peak table is within 125% of the lowest peak in that set; and where the next adjacent pulses (viz, two away) to that same highest amplitude pulse are greater then 66% of the amplitude of that highest peak pulse of said adjacent pulses in the pulse table. The reference level is the average of the peaks of the pulses in the set. It has been found in accordance with the invention that the proportionality between the reference level and the amplitude corresponding to the diastolic event is 75% of the reference level. The proportionality in the case of the systolic event has been found in accordance with the invention to be 45% of the reference level. The pulses corresponding to the systolic event are found by searching in the pulse table away from the highest amplitude pulses in the direction of higher cuff pressures for a pair of successive pulses, both of which are less than the systolic threshold level. The pulse prior to the occurrence of this pair is taken as occurring at the time of the systolic event. The pulse which is taken as occurring at the time of the diastolic event is obtained by searching the pulse table away from the set of highest amplitude pulses toward lower cuff pressures until a pair of pulses are found which are lower than the diastolic threshold level. The pulse prior to the occurrence of this pair is taken as occuring at the time of the diastolic event. Outputs are provided from the cuff table of the digital signals which correspond to cuff pressures concurrent with the pulses occurring at the time of the systolic and diastolic events. These outputs may be displayed as on a digital readout so as to indicate the systolic and diastolic pressures, one above the other. These outputs may also be transmitted to remote storage or auxiliary display apparatus.

Incorrect operations and other artifacts are detected in response to the location of the pulses in the pulse table representing the systolic and diastolic events and the time between pulses. In the event that a peak reference level cannot be obtained from the signals acquired during a measurement cycle or the pulses corresponding to the systolic or diastolic events do not satisfy the other criteria, an error is indicated on the display.

Pulse rate is obtained in terms of the time to acquire a group of pulses in the pulse table. This group may be located on the side of the highest amplitude pulses toward lower cuff pressures when the measurement is made on the deflation part of the cycle. Rate is computed in terms of the interval required to acquire these pulses. An output corresponding to the rate may be displayed alternatively with the blood pressure or on a separate display if desired.

An instrument embodying the invention may use a programmed data processor which has a memory for storing a program and the data corresponding to the digital signals in each of the tables. The data processor has means for providing each of the operations requisite to the measurement of the blood pressure in terms of the pulses which have amplitudes which are related to the percentages of the reference level mentioned above, as well as for the detection of artifacts and incorrect operation. The method may also be carried out by recording the signals representing the cuff pressures and the pulse train graphically, as on a strip chart and analyzing the pulses and providing outputs representing the diastolic and systolic pressures and the pulse rate in accordance with the method herein described. Alternatively, a system for processing the signals on an analog basis may be used to provide outputs representing the blood pressure measurements. Apparatus utilizing a programmed data processor, particularly in the form of a microcomputer, is presently the preferred embodiment of apparatus for practicing the invention.

The foregoing and other objects and advantages of the present invention as well as the preferred embodiment thereof and preferred mode of practicing the invention will become more apparent from the following description when taken with the accompanying drawings in which.

Figure 7:
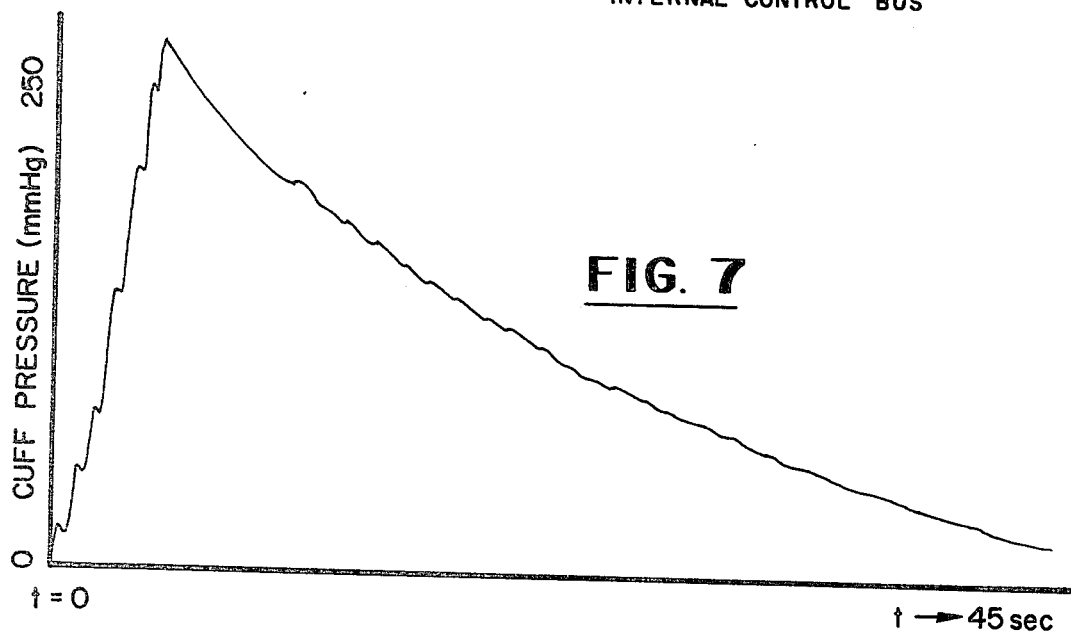
Figure 8:
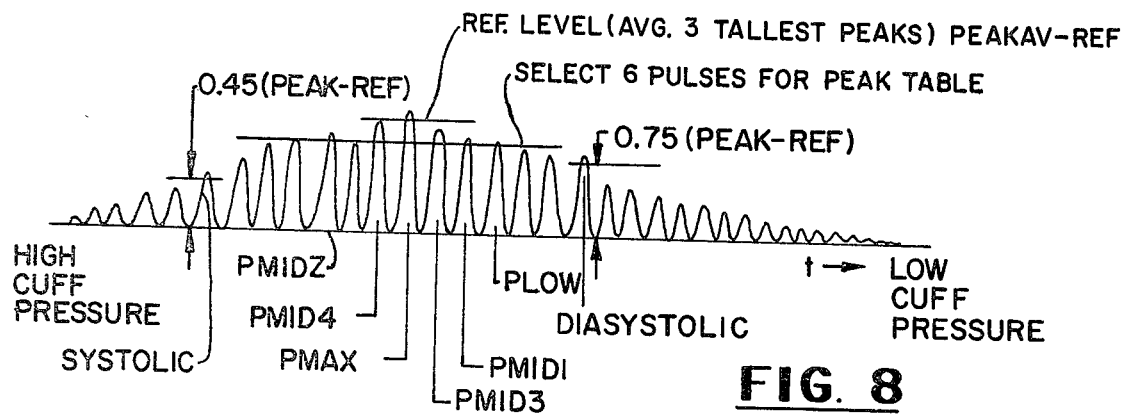
Figure 9:
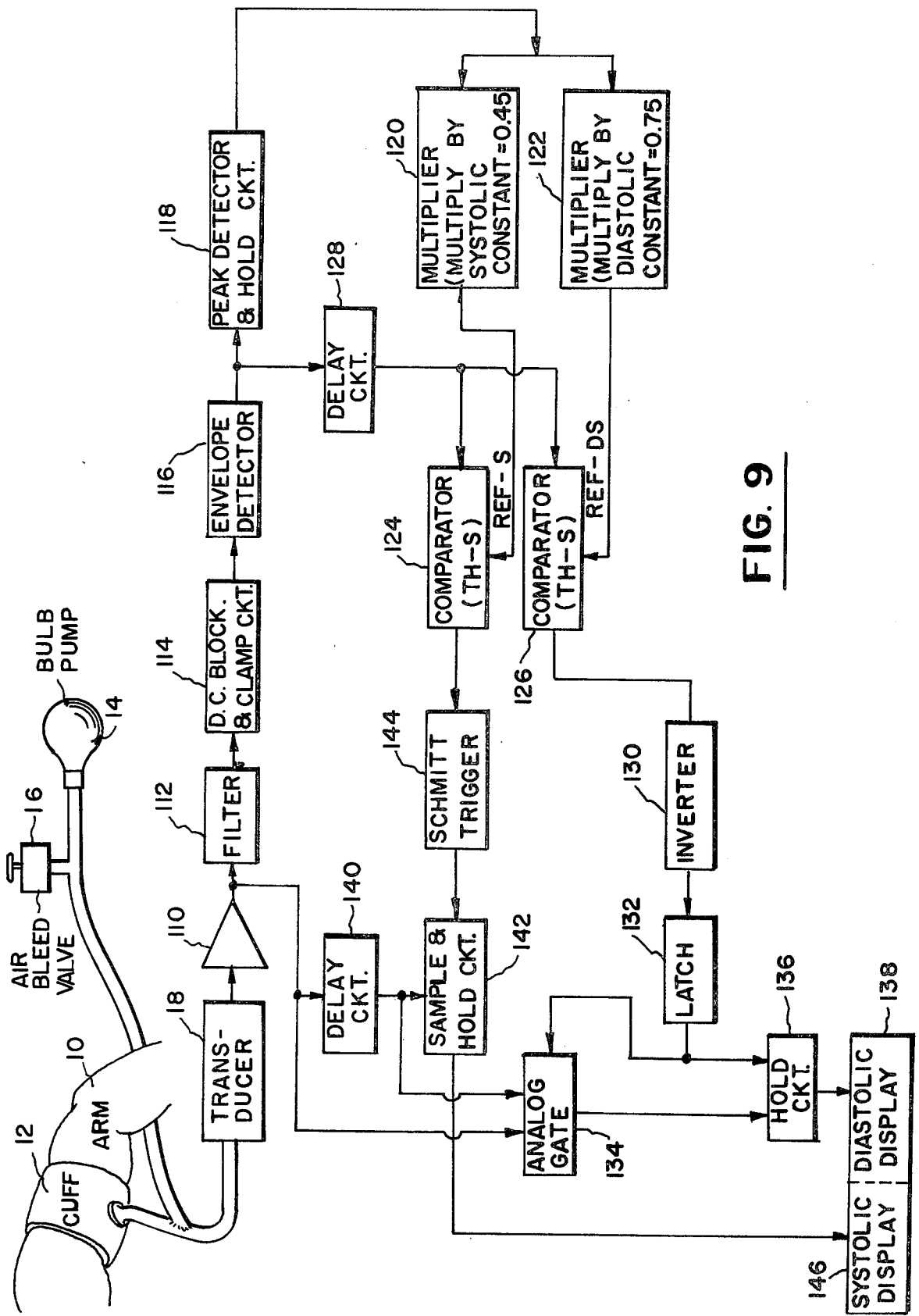

FIGS. 6A through 6H constitute a flow chart of the operations which the apparatus is conditioned to perform in the measurement of blood pressure and pulse rate in accordance with the presently preferred embodiment of the invention;

FIG. 7 is a waveform showing the cuff pressure as it varies with time during a measurement cycle;

FIG. 8 is a waveform diagram showing the oscillometric pulse train which is produced and utilized in accordance with the invention; and FIG. 9 is a block diagram of apparatus utilizing analog circuitry for the measurements of blood pressure in accordance with the invention.

Figure 1:
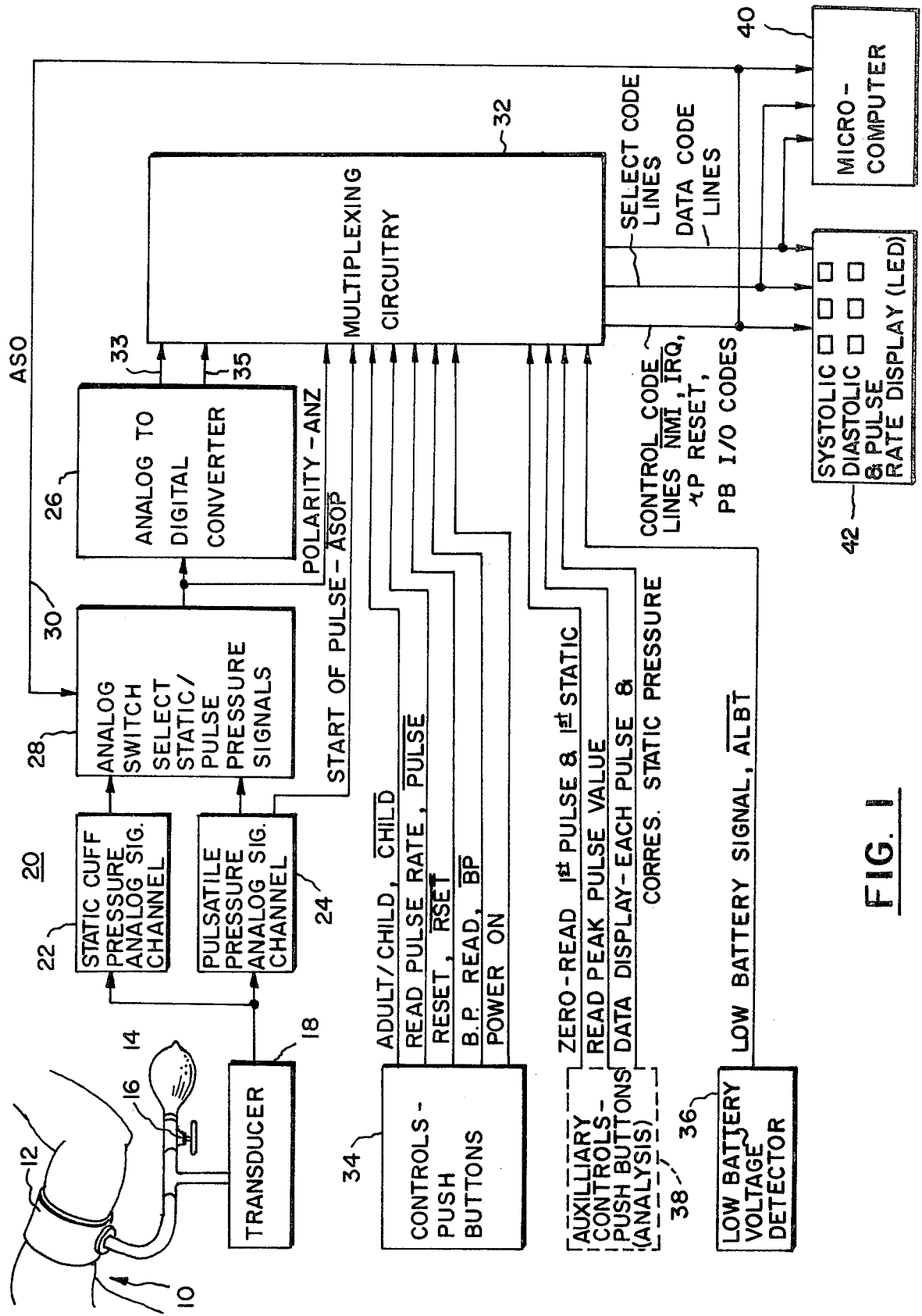
FIG. 1 is a block diagram of apparatus in accordance with a preferred embodiment of the invention which apparatus practices the method of the invention in accordance with the presently preferred embodiment thereof.

Referring more particularly to FIG. 1, there is shown the upper arm 10 of a patient around which is fastened a blood pressure cuff 12. While the arm is most conveniently used, other body members may be used (e.g., the thigh). The cuff is inflated through the use of a bulb which acts as a pump 14. Deflation of the cuff occurs when a valve 16 is opened to bleed the air from the cuff. As the description proceeds, it will be apparent that the inflation and deflation of the cuff may be automated if desired under the control of signals which are generated in the operation of the apparatus.

The pressure in the cuff upon which the pulsations due to the pumping action of the heart are superimposed are sensed by a transducer 18 which may be a piezoelectric element which preferably is selected so that its output voltage does not drift below zero voltage with time. The transducer 18 thus provides an electrical signal which is proportional to the cuff pressure.

This signal is processed by analog circuitry 20 which separates the signal into two signals, one of which is proportional to the static pressure in the cuff, and the other to the pulsatile pressure in the cuff. The analog processing to separate the signals takes place in a static pressure channel 22 and in a pulsatile pressure channel 24. The pulsatile pressure channel 24 provides a train of pulses each corresponding to a successive pulsation of the heart. The start of each pulse is detected and the result of this detection is a start of pulse control signal $\overline{\text{ASOP}}$. The signals are active or asserted in this exemplary embodiment in the low state, as indicated by the bar over the signal notation.

The analog signals from the static cuff pressure channel 22 and the pulsatile pressure channel 24 are selectively applied to an analog to digital converter 26 by an analog select switch 28. A control line 30 applies control signals to the switch 28, which control signals are generated in response to the start of pulse command $\overline{\text{ASOP}}$. The switch 28 is conditioned to the state where the signals from the pulsatile channel 24 are applied to the analog to digital converter in response to an $\overline{\text{ASOP}}$ control signal. The state of the switch 28 is, in the absence of the $\overline{\text{ASOP}}$ signal, such that the static cuff pressure signal from the channel 22 is applied to the analog to digital converter. The converter 26 outputs digital signals corresponding to the cuff pressure and pulsatile pressure signals on data lines 33. The converter also outputs digit strobes concurrently with the digital signals but on separate output lines 34. One of the lines 35 outputs a signal upon the end of a conversion cycle. This signal controls the timing of the control signal which is applied to the select switch 28 by way of the control line 30. Accordingly, digital signals are successively outputted by the converter 26 which correspond to the static cuff pressure signal and to the pulsatile pressure signal at substantially the same time.

The polarity of the analog signals at the output of the switch 28 are used to provide a control signal which represents the polarity of the analog signals outputted by the switch 28. Signals having a negative polarity are indicative of incorrect operation of the transducer 18 and are not useful in the measurement of blood pressure. Accordingly the control signal ANZ representing an analog signal which is of negative polarity is generated and used to inhibit the transfer of data signals to the apparatus which obtains the blood pressure measurement whenever a negative analog signal appears at the output of the switch 28.

The output of the analog to digital converter is applied to multiplexing circuitry 32. Inputs to the multiplexing circuit 32 are also the $\overline{\text{ASOP}}$ and the ANZ control signals. The instrument is supplied with controls 34 which may be in the form of push-button switches. Each of these switches generates a control signal. These control signals indicate that the power to the instrument as may be obtained from a battery or the power line, is on; that the blood pressure measurement is to be read (called BP); that the apparatus is to be reset (called $\overline{\text{RSET}}$); that the pulse rate is to be read out (called $\overline{\text{PULSE}}$); and that the instrument is to be conditioned to be used to measure the blood pressure of a child rather than an adult (called $\overline{\text{CHILD}}$). In the event that a battery is used as a power source, it is desirable to provide a low battery voltage detector 36 which generates a control signal $\overline{\text{ALBT}}$ when the battery voltage is below limits for the reliable operation of the apparatus. Auxiliary inputs may be provided for diagnostic purposes, i.e., for testing the apparatus when it is fabricated or for maintenance purposes. Auxiliary control pushbutton switches 38, which may be located in a tester rather than in the instrument itself, generate control signals which condition the apparatus to read out and display certain of the signals which are acquired and stored in the operation of the apparatus.

The apparatus also includes a programmed data processor which in the preferred embodiment is a microcomputer 40 and a read out or display 42. The display is shown as having provision for six digits in two rows of three digits. The top row of the display is used to indicate the systolic pressure, while the lower row indicates the diastolic pressure and pulse rate. Both the systolic and diastolic pressures are simultaneously displayed when the blood pressure read push button is actuated. The apparatus is operative to store the blood pressures until the reset push button is actuated or a period of time elapses, say 15 seconds, during which no readouts are selected. Accordingly, the human error due to misinterpretation of an evanescent measurement as is produced with conventional sphygmomanometers is avoided.

The microcomputer 40 consists of a microprocessor integrated circuit, an input/output or interface integrated circuit, and one or more memory integrated circuits. Such microcomputers and their operation are described in manuals published by the manufacturer thereof. For example, see the "INTEL MCS-40 User's Manual for Logic Designers", or the "INTEL 8080 Microcomputer Systems User's Manual", which are published by INTEL Corporation, Microcomputer Systems, 3065 Bowers Avenue, Santa Clara, Calif. 95051, and the "Hardware Programming Cross Assembler and Emulator Manuals" and the "Systems Handbook", published by MOS Technology, Inc., 950 Rittenhouse Road, Norristown, Pa. 19401. The microcomputer 40 is connected to the multiplexing circuitry 32 and display 42 by way of data code lines, select code lines, and control code lines. These lines are sometimes also referred to as buses. The arrangement of the control lines depends upon the artchitecture of the microcomputer. The programming of microcomputers also depends upon the architecture of the selected computer. The instructions and method of programming of the INTEL microcomputers is for example described in the above referenced User Manuals, and the instructions and method of programming of the computers sold by MOS Technology are described in their manuals, which are referenced above. The disclosure in this application will enable a programmer having ordinary skill in the art to produce an appropriate program for whichever computer is used in the apparatus, whether it be a computer sold by INTEL, MOS Technology, or some other microcomputer, a mini-computer, or other programmed data processor.

The control lines provide $\overline{\text{NMI}}$ (non-maskable interrupt), $\overline{\text{IRQ}}$ (interrupt), uP reset and PB input/output codes. The interrupt commands are functions of the analog to digital conversion cycle, while the microprocessor reset and PB codes are functions of the control inputs from the controls 34 and 38, the low battery voltage detector 36, and the $\overline{\text{ASOP}}$ and ANZ lines. The data and select codes are inputted through the multiplexing circuit 32 to the microcomputer.

The microcomputer inputs and outputs data and select codes on lines having three states. The multiplexing circuit 32 data and select code outputs are placed in the high impedance or third state during the display cycle and for brief intervals before and after this cycle so as to enable the microcomputer to use the same data and select lines as the output lines to the display 42.

Overall system timing is by means of a master clock pulse source which is connected to the converter 26, the multiplexing circuitry 32 and the microcomputer 40.

Figure 2:
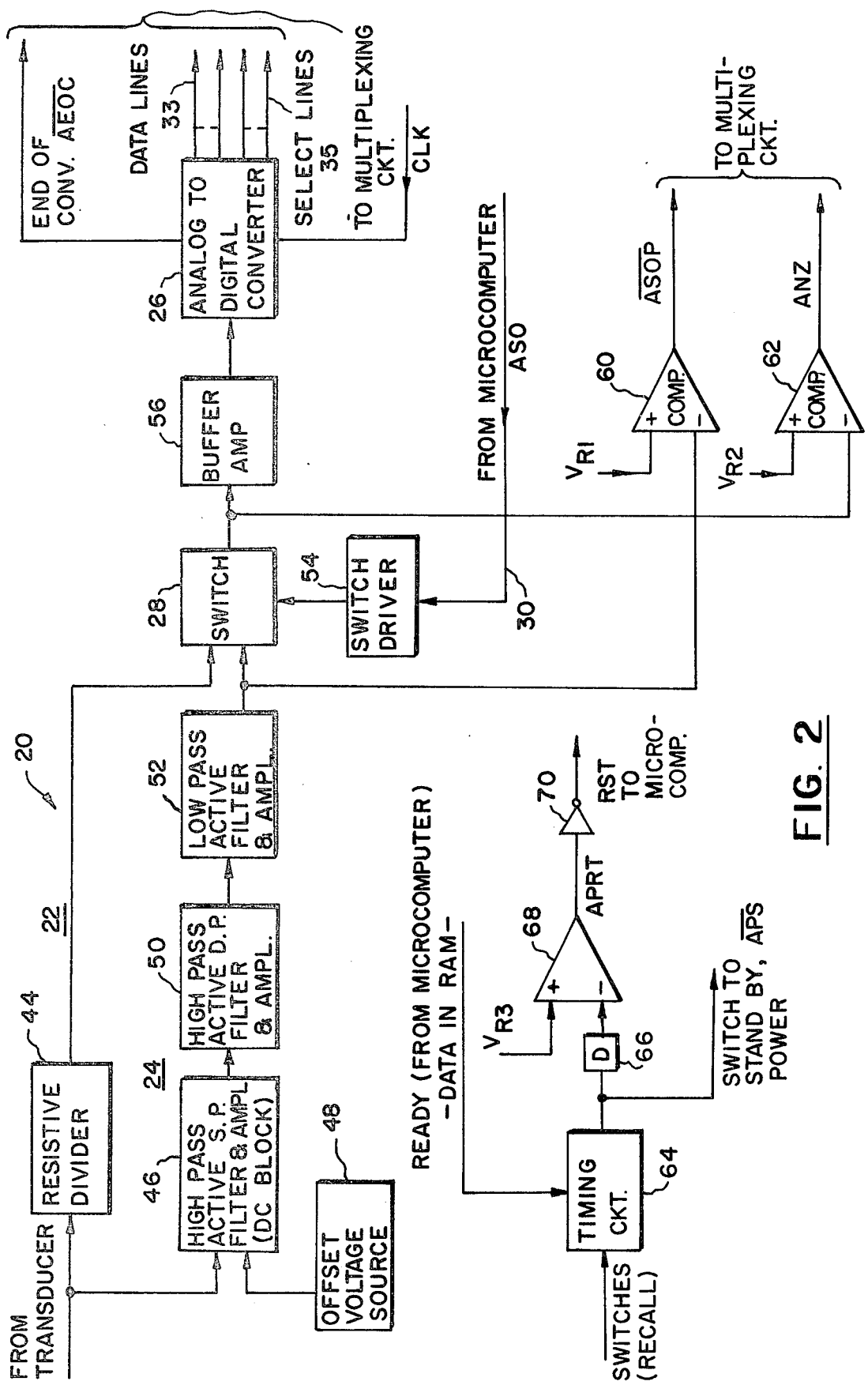
FIG. 2 is a block diagram of the analog signal processing circuits, the analog to digital converting circuits, and a portion of the circuits for providing control signals which are used in the apparatus shown in FIG. 1.

The analog circuitry 20 is shown in greater detail in FIG. 2. The cuff pressure channel 22 contains a resistive divider circuit 44 which adjusts the magnitude of the cuff pressure signal such that its maximum value will be within the range of the analog to digital converter 26.

The pulsatile pressure channel 24 receives the signal from the transducer at the input of a high pass active single pole filter and amplifier circuit 46. This circuit may be implemented with an operational amplifier having a blocking capacitor at its input which also is part of the filter. An offset voltage may be added to the input signal after it passes through the blocking capacitor to safeguard against the clipping of the input signal. The offset voltage is supplied to the high pass active single pole filter and amplifier 46 from an offset voltage source 48. The filter cutoff is selected so as to eliminate any fluctuations in the base line voltage of the pulse train, a low frequency cutoff (−3 dB point) of 0.6 Hz is suitable.

The amplified pulse train is then applied to another active filter and amplifier stage 50 which has a high pass double pole filter characteristic. This stage may be implemented by an operational amplifier with feedback and capacitive input circuits so as to provide the double pole filter characteristic. The stage 50 removes the offset introduced by the offset voltage source 48 and yields the output pulses in the form of unipolar pulses (e.g., all positive). Suitably the double pole high pass filter has a low frequency cutoff at approximately 0.34 Hz as measured at the −6 dB point. The output of the double pole filter and amplifier stage 50 is applied to a low pass active filter and amplifier 52 which serves to reduce the noise content of the pulsatile signal and smooth the signal for analog to digital conversion. This stage 52 may also be implemented by an operational amplifier and suitable feedback circuits. The high frequency cutoff may suitably be 6.4 Hz at the −3 dB point. The filter and amplifier stages in the pulsatile channel 24 form a bandpass filter which provides unipolar pulses having a stable zero base line to the switch 28.

The switch 28 may be provided by a CMOS integrated circuit which is driven by a switch driver stage 54 which may be a transistor amplifier. The control signal ASO from the microcomputer controls the selection of either the cuff pressure signal from the channel 22 or the pulsatile pressure signal from the channel 24 by the switch 28. A buffer amplifier 56 accomodate attenuation due to the switch 28.

The start of each pulse is detected by a comparator 60 which outputs the $\overline{ASOP}$ control signal when the pulse amplitude exceeds a reference level. As mentioned above, the $\overline{ASOP}$ control signal results in the generation of the ASO signal such that the switch 28 will be controlled to apply the cuff pressure signal when there is no pulse and the pulse signal to the buffer amplifier 56 when a pulse is present.

The signal at the output of the switch 28 is applied to another comparator 62. A reference voltage $V_{R2}$ slightly higher (e.g., 10 mv) than the circuit reference voltage (e.g., ground) is applied to the direct input of the comparator 62 while the signal is applied to the inverted input thereof. Accordingly, if the signal outputted by switch 28 is below the $V_{R2}$, the signal is deemed to be of negative polarity and the ANZ control signal goes high which serves to inhibit the data from the converter 26 as will be explained hereinafter.

The analog to digital converter 26 outputs a control signal $\overline{AEOC}$ when a conversion is complete. Each conversion is accompanied by a code which may be in BCD (binary coded decimal) format on the data lines 33 which is a digital signal representing the amplitude of the analog signal applied to the converter 26 from the output of the buffer amplifier 56. Each BCD digit is accompanied by a different code on the select lines 35. Each of these lines carries a different digit strobe and serves to identify the BCD digits generated upon each conversion. For example, the BCD format may consist of three digits (3 bytes) which are outputted successively. The digit strobes on three select lines identify the BCD digits. These select lines are used for multiplexing the data signals and the control signals from the push button controls (34 and 38) as well as the $\overline{ASOP}$ and $\overline{ALBT}$ control signals in the multiplexing circuitry 32 (see FIG. 1).

Power for the system may be provided from the power lines or from a battery. A rectifier power supply is used to convert the AC power line voltage to direct current voltage. This rectifier supply may be connected to a common junction with the battery supply. A series diode in the battery circuit may be used to sense when the rectifier power supply voltage drops below battery voltage, as when the plug to the power line is disconnected, such that the battery will automatically be inserted into the circuit to provide the power for the instrument. An ON/OFF switch connects the battery or the supply to regulator circuits.

In order to conserve power, it is desirable to use separate circuits to supply operating voltage to the analog circuitry and the digital circuits which are active while the signals from the transducer are analyzed in the course of a measurement, and a separate circuit to provide power for the random access memories which store the data in the microcomputer. It is therefore desirable that the circuits used to supply power to the analog circuits, the digital circuits, and the display which are active in a measurement, not be switched off until the data is stored in the memories. It is also desirable to reset all of the circuitry and clear the memories when power is switched off. Before the system can switch to a standby condition with only the circuitry which powers the memories operative, the microcomputer provides a ready signal to a timing circuit 64 which may be a flip-flop set by the ready command. The timing circuit then provides a control signal, $\overline{APS}$ which operates to switch off those circuits which are only active in performing a measurement. The instrument then is on standby power. In order to switch back to full power, any of the control switches, say for example, the blood pressure read push button switch, may be actuated. This signifies a recall and resets the flip-flop in the timing circuit 64. The system will then switch back to full power operation. The $\overline{APS}$ signal is applied to a delay circuit 66 which may be a resistor capacitor discharge circuit, to a comparator 68. After a period of time, the voltage to the comparator 68 will rise above the reference voltage $V_{R3}$ (the reference voltage being obtained from the same power circuit that supplies the memories) so as to provide a control signal APRT which is inverted in an inverter 70 and applied to reset the microcomputer by applying a reset command thereto. Then the system will be cleared and ready for a new measurement if a recall is not indicated within the time delay set by the circuit 66.

An indication may be provided on the display 42 when the instrument is in the standby mode as by using the output of the timing circuit 64 to illuminate a portion of one of the digits of the display, say the digit which is used to show a decimal point. The display of a decimal point without any other digital information thus indicates that the instrument is in standby.

The analog to digital converter 26 may suitably be implemented with a pair of integrated circuits, one of which produces the $\overline{AEOC}$ signal and a ramp command which is converted into the digital signals on the data and select lines, one such pair of analog to digital converter integrated circuits is available from Motorola Inc., of Chicago, Ill. and Phoenix, Ariz., their Types MC-1405 and MC-14435. The same clock generating circuits as supply the clock signals in the microcomputer 40 also are applied to the analog to digital converter 26 such that the time when data and the digit strobes are available from the analog to digital converter 26 and the times when the microprocessor routines are carried out under program control are in phase synchronization within the tolerances for the particular microcomputer components used in the apparatus.

The analog filters 46 and 50 can be eliminated by use of digital filtering techniques. For example, the characteristics of the present analog filters can be transformed into digital filters using the design techniques in (for example) Chapter 5 of A. V. Oppenheim and R. W. Schafer, *Digital Signal Processing* Prentice-Hall, Inc., N.J., 1975. Using digital filtering, the transducer signal may be passed through a low-pass filter, say with a $-3$ dB point at about twice the highest frequency of interest (the low-pass ($-3$ db) point may be at approximately 20 Hz). The output of the low-pass filter will be amplified and A/D converted. The digital signal from the A to D converter is then inputted to the microcomputer where the digital filtering may be done. $\overline{ASOP}$ will therefore be generated within the computer instead of externally, as shown in FIG. 2.

Figure 3:
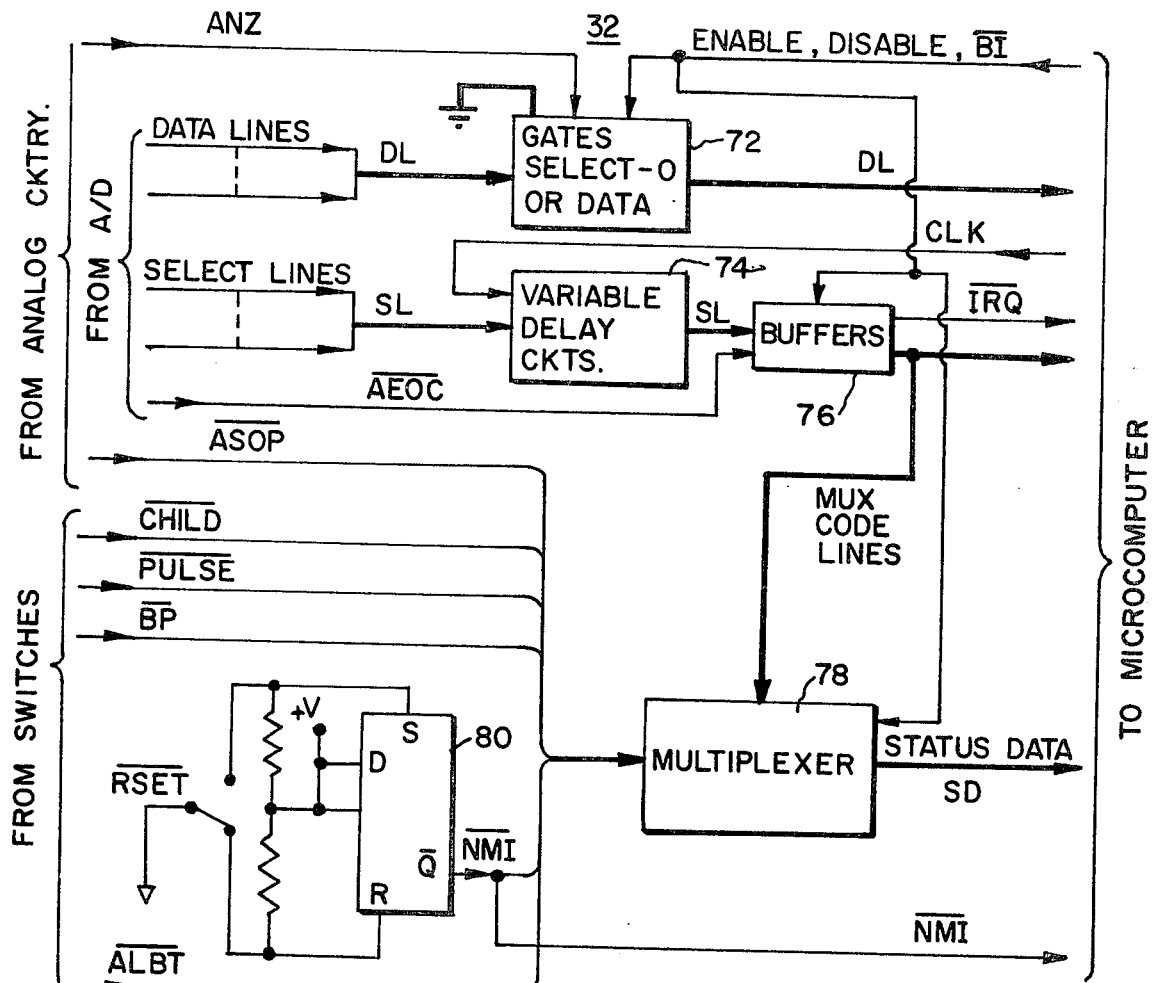
FIG. 3 is a block diagram of the multiplexing circuitry of the apparatus shown in FIG. 1.

The multiplexing circuitry 32 is illustrated in FIG. 3. The data lines DL from the analog to digital converter and the ANZ control signal are applied to gates 72. An enable/disable command, $\overline{BI}$ which is generated in the microcomputer is also applied to the gates 72, and when it is high serves to disable or inhibit the gates 72. The command $\overline{BI}$ when high also blanks the display and places the data lines in the third or high impedance state, so that the microcomputer can use the same lines to handle data and to output data to the display. When the ANZ signal is high, the gates output ground to the data lines such that false codes are not generated and a signal below the zero base line is indicated as a zero amplitude signal.

The select lines SL which carry the digit strobes are applied together with the clock signal from the microprocessor to variable delay circuits 74. The outputs of these delay circuits are the select lines, the timing of which is controlled with respect to the clock in the delay circuit 74, such that the timing of the digit strobes on the select lines and the data on the data lines are in phase synchronization with the read period of the microcomputer, as is set by the clock. The variable delay circuit 74 may be implemented by RC delay networks for each of the select lines.

The select lines and the line carrying the end of conversion signal $\overline{AEOC}$ go to buffers 76 which may be suitably integrated circuit (IC) high impedance buffers in a single IC chip. The enable/disable line is applied to the reset lines of the buffers 76 so as to tri-state these lines and thereby disable the outputs from the buffers 76 when the display is not blanked. The $\overline{AEOC}$ signal is transferred through the buffers 76 without tri-stating and is outputted by the buffers as the interrupt $\overline{IRQ}$. The digit strobes are outputted from the buffers as multiplex codes and applied to a multiplexer circuit 78. The select lines are also inputted to the data register of the interface (I/O) unit of the microcomputer as will be discussed hereinafter.

The multiplexer 78 may be implemented by separate multiplexer circuits, one of which multiplexes the ALBT control signals and signals from the analog to digital converter indicative of an over-range output and the most significant digit. The other multiplexer circuit multiplexes the control signals ASOP representing the start of a pulse of the pulse train in the analog pulsatile signal; $\overline{CHILD}$ and the blood pressure and pulse read commands $\overline{PULSE}$ and $\overline{BP}$ which are produced by the switches. In order to avoid erroneous interrupts due to contact bounce when the reset switch is actuated, a D-type flip-flop 80 is used to provide the $\overline{NMI}$ output when the reset switch is actuated to ground the reset R input of the flip-flop 80.

The $\overline{NMI}$ command is applied directly to the microcomputer as well as to the multiplexer. The multiplexer outputs status data, SD, to the microcomputer on status data lines; different status data is outputted at the end of each conversion cycle. For instance, the multiplexer outputs on one of the status data lines the control signal indicating the $\overline{CHILD}$ function when the first bit of the strobes on the select lines is low and the other bits on the select lines are high. Similarly, all of the other function control signals, the ALBT and ASOP control signals as well as the factory test and maintenance control signals from the auxiliary control push buttons 38 (FIG. 1) are multiplexed for different select codes which are applied on the mux or multiplex control lines to the multiplexer 78.

Figure 4:
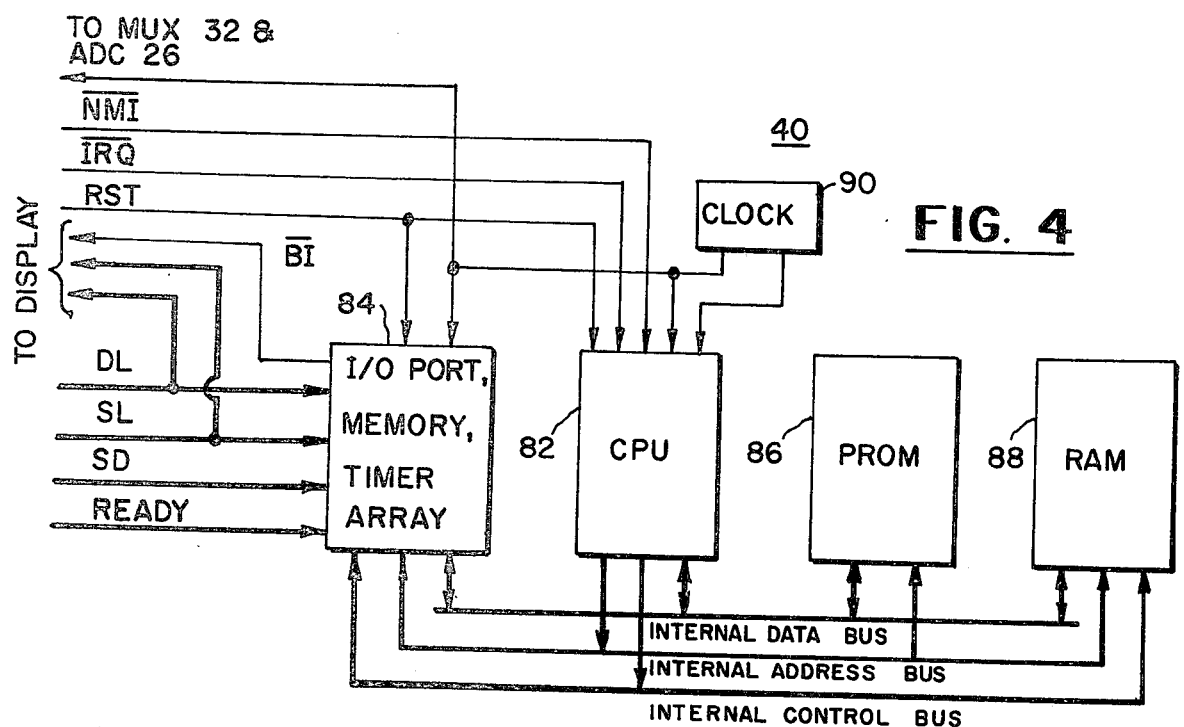
FIG. 4 is a block diagram of the microcomputer which is shown in FIG. 1.

The microcomputer 40 is shown in greater detail in FIG. 4. It includes a central processing unit or CPU 82 which is also called a microprocessor. The CPU 82 is connected by way of an internal data bus, an internal address bus, and an internal control bus, to an interface unit called an I/O port 84. This port may contain internal memory and timer arrays. Also in the microcomputer is a read only memory, which may be a programmable read only memory or PROM device 86. It is in this device that the program is stored. The microprocessor also contains a random access memory or RAM 88. This random access memory may be provided by one or more units in the system therein described. The CPU 82 and the I/O port 84 receive timing or clock pulses from a clock generator 90.

The microcomputer may suitably be implemented in the form shown in FIG. 4 by a type MCS 6503 microprocessor which serves as the CPU 82 and a type MCS 6530 I/O port unit 84. This unit 84 in one chip contains random access memory, read only memory, an interval timer array, and a number of registers for data and control bits. MCS 6111 random access memories may suitably be used to provide the RAM 88, and 3604L-6 read only memory devices can suitably be used as the PROM 86. The 6111, 6503, and 6530 devices are integrated circuits available from MOS Technology, and the 3604 is an integrated circuit available from INTEL.

Other microcomputer units from other manufacturers may, of course, be used. The MOS Technology and INTEL devices are mentioned above as being exemplary of a suitable microcomputer arrangement which should facilitate the understanding of the exemplary apparatus herein described.

The CPU 82 steps through the program, which will be described in detail hereinafter in connection with FIG. 6, addresses the I/O port 84 and the internal memory therein, and the RAM 88 and PROM 86. Data is transferred back and forth between the CPU, the I/O port, the PROM 86 and the RAM 88 over the internal data bus which in the case of the MCS 6503 is an eight bit data bus. Addresses generated in the CPU are transmitted over the internal address bus which carries twelve bits between the I/O port, the CPU 82, and the PROM 86. The addressing of the RAMs when the MCS 6111 are used, may be by ANDing the inversion of the higher order address lines (A9, A10, and A11) which, when all are "1"s, notes that RAM is being addressed and constitutes a chip enable control signal. A chip enable power down signal may be generated together with the standby and reset signals APS and APRT (see FIG. 2) and applied to the chip enable inputs of the RAM so as to prevent the RAMs from being addressed when the apparatus is in the standby mode. This protects the data in RAM during the standby cycle and permits the data to be used to provide a display when a recall is selected. Inasmuch as the MC6111s are organized as 256 sequential address locations of four bits each, two chips are used to constitute a RAM which has storage for an eight bit byte. Four 6511 chips thus provide storage for 512 bytes. Each INTEL 3604L-6 PROM has storage for 512 eight bit bytes. Three such chips are used to provide 1536 address locations. These locations are selected by coding nine of the address lines of the bus, A0 through A8 and then A9, A10, and A11, or the inversions thereof on PROM address lines so as to select the addresses on different ones of the PROM chips.

The I/O port 84 provides fifteen lines which are connected to the external inputs. Four of these inputs are the data lines DL. The select lines are connected to four other inputs. These may be the PA register of the 6530 I/O port 84. The status data lines from the multiplexer 78 are inputted to others of these fifteen lines which may be the PB register inputs of the MCS 6530. Other of the PB lines are used to provide the ready signal and the blanking signal $\overline{BI}$. These lines may be read by the CPU 82 or placed in output mode and data is sent out in parallel. Thus data is sent out from the port to the display 42 on the same lines as are connected to the data line and select line inputs. The $\overline{BI}$ line is also applied to the display for blanking purposes.

The I/O port 84 and the CPU also receive the reset RST inputs. The IRQ and NMI commands are applied directly to the CPU. The clock generator 90 provides one of the clock phases to the I/O port for timing control.

The read/write commands are outputted by the CPU on the internal control button to the I/O port and the RAMs. The address lines A9 to A11, which select either RAMs or PROM, may be considered part of the internal control bus.

Part of the read only memory (ROM) may be provided by the one kilobyte of ROM contained in the MCS 6530 I/O port or in the external PROM or ROM devices 86.

Figure 5:
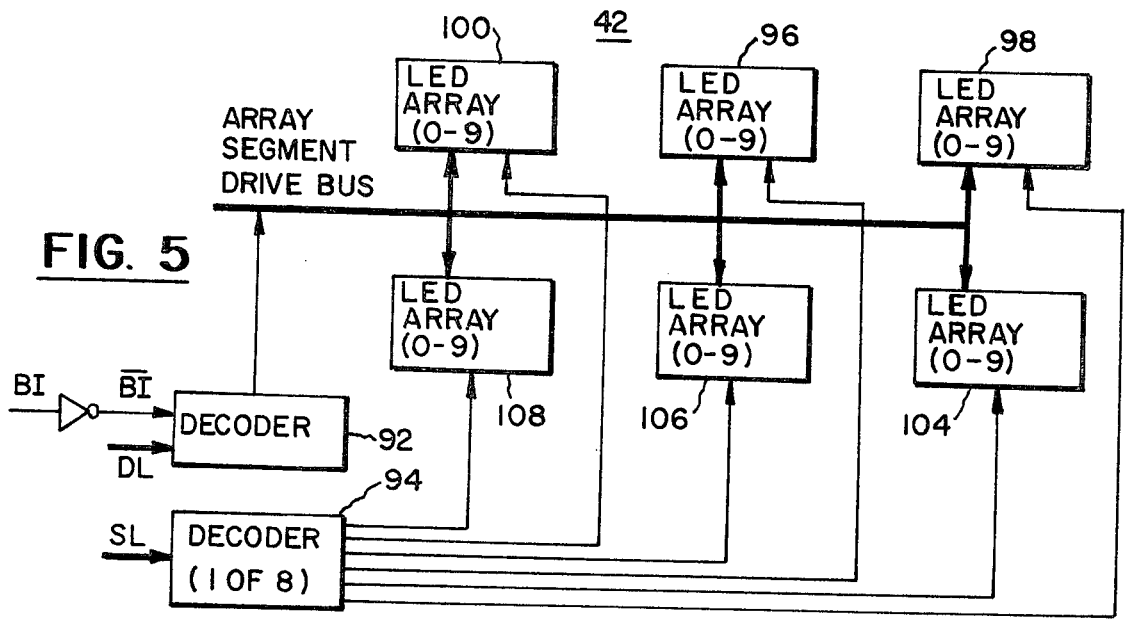
FIG. 5 is a block diagram of the light-emitting diode (LED) display shown in FIG. 1.

The display 42 is shown in simplified form in FIG. 5. It has several functions, namely to display the numerical results, either blood pressure or pulse rate; to provide a display indicating the functional status of the instrument (i.e. to indicate erroneous results) and to test the status of the instrument either for diagnostic or maintenance purposes; and to indicate that the instrument is in the standby mode. The display of numerical results (blood pressure or pulse rate) and functional status (error or diagnostics) is provided by decoders 92 and 94. The decoder 92 is a hexadecimal decoder inasmuch as the data is handled in the microcomputer in hexadecimal code. This decoder receives the four data lines and the blanking signal which is a high level during the read cycle and thus requires inversion. The $\overline{BI}$ input automatically blanks the display. A blanking code of (00) may also be accomplished in a one out of eight decoder 94 which receives the select lines when the select digits, PA 4 through PA 6 from the MCS 6530 I/O port 84 (FIG. 4) when one of the digits is selected and that digit is to be blanked. One of the select lines, the PA 7 I/O port line, may be used to select one of the digits, say the digit selected by the LED array 96 so as to indicate a decimal point, thus connoting that the system is in the standby power mode.

The display consists of six LED arrays, three of which, 96, 98, and 100, are in the top row of the display and three of which, 104, 106, and 108, are in the bottom row of the display. Digit selection is controlled by the one out of eight decoder 94 which is controlled by the PA 4, PA 5, and PA 6 lines of the select lines from the MCS 6530 which constitute a three bit binary code signal. The hexadecimal decoder 92 drives the array segment bus which energizes the LEDs which constitute the arrays 96 through 108. As the program scans the LED arrays, the digits are driven successively and at a sufficiently high rate such that the display remains flicker free. When an error is indicated, the array 106 is selected so as to blink the letter "E".

Referring next to FIGS. 7 and 8, there are shown (in FIG. 7) a waveform of the cuff pressure signal with respect to time, and a waveform of the pulsatile pressure signal or pulse train (FIG. 8). These are the signals which are provided by the cuff pressure analog signal channels 22 and the pulsatile pressure analog signal channel 24. The cuff pressure signal contains the static cuff pressure on which the variations in pressure due to the pumping action of the heart are superimposed. The heart pumping actions appear as pulsations which are a few millimeters of mercury in height. Each pulsation begins prior to a systolic event and terminates after the occurrence of the diastolic event.

The pulsatile signal or oscillometric pulse train, with the static pressure or bias removed, is shown in FIG. 8. The static pressure will, of course, vary as the pressure is allowed to bleed from the cuff. Such variation in pressure is much slower than the pulsatile pressure variations due to the pumping action of the heart. Accordingly, the static cuff pressure can be considered to be a bias.

FIG. 8 also shows the method provided in accordance with the invention for selecting the systolic and diastolic pressures. The train of pulses as shown in FIG. 8 and the corresponding static pressure variation as shown in FIG. 7 are obtained by placing the cuff over an extremity, preferably the upper arm or upper leg, in a position so that its inflation will occlude a major artery, which in the case of the upper arm will be the brachial artery. The cuff is inflated to above the systolic level and the pressure is allowed to bleed from the cuff as by opening up the bleed valve. The cuff slowly deflates. A suitable deflation rate is 3 to 6 millimeters of mercury pressure per heart beat. The waveform of the static cuff pressure will then have the appearance of the waveform shown in FIG. 7 while the pulse train will have the appearance shown in FIG. 8.

The three tallest or highest pulses in the train, which need not be adjacent to each other in the pulse table, are then selected. These are the pulses indicated at PMAX and the two pulses next adjacent thereto which are shown capped by the heavy line to which the legend "REF. level" (average of three tallest peaks) PEAKAV-REF is applied. These three pulses are a set of a group of pulses which can be considered as belonging to a peak table containing six of the highest amplitude pulses. These pulses are stored and used in obtaining the blood pressure measurement by means of the microcomputer 40 (FIG. 1) as was explained above and will be discussed further hereinafter. The peak table is, of course, stored in graphical form in the waveform of the pulse train shown in FIG. 8.

In order to assure that the three tallest pulses are real pulses and not artifacts, introduced say by external bumping of the cuff or muscle flexion, the tallest pulse and the pulses closest thereto in amplitude are tested. These are, in FIG. 8, the PMAX, PMID4, and PMID3 pulses. This set of adjacent pulses in the peak table is such that the tallest pulse in the set is equal to or less than 125% of the shortest pulse. When a set of pulses satisfies this criteria, it is tested so as to satisfy another criteria, namely that the pulses in the pulse table next adjacent or two away from the highest or tallest pulse of said set, must be greater than 66% of the said tallest pulse.

If the peak table is exhausted (no more pulses in the table) before the test can be satisfied, an error indication (a blinking E) will be displayed. It is a feature of the invention to give an error signal, rather than an inaccurate result.

The average or arithmetic mean of the peak amplitudes of the three tallest pulses which pass the above tests is the reference level which is referred to as PEAKAV-REF.

Once a reference level has been found, the systolic pressure is determined by searching upward in the direction of higher cuff pressure from one of the tallest pulses (viz. from the pulse indicated as PMID2, which is the second from the lowest pulse, called PLOW, in the peak table and is approximately at the center of the peak table). The search is continued in a direction of higher cuff pressure until a set of three adjacent pulses is found. This search is first for two pulses of amplitude less than a systolic threshold level, then for the third pulse which is greater than or equal to the systolic threshold level. This third pulse must be adjacent to the two pulses, but closest to the tallest pulse (i.e. to PMID2). In other words, the last pulse of the set which is equal to or greater than the systolic threshold level is found by backing up toward the tallest pulse from the pair of pulses which are below the threshold. The third pulse of the set is at the onset of the systolic event. It has been determined experimentally based on clinical data that the systolic threshold level is 45% of PEAKAV-REF and that this first pulse (equal to or above the systolic threshold level) identifies the onset of the systolic event.

Similarly, the diastolic threshold is 75% of the reference level. The diastolic event is obtained by selecting the pulse before two adjacent pulses below the diastolic threshold which are found by searching away from the highest amplitude pulses in the direction of lower cuff pressures (viz, toward lower cuff pressures from PMID2). A set of three adjacent pulses are therefore found as is the case for the systolic pressure pulse.

Inasmuch as three pulses are found to identify the diastolic event, the event will not usually be detected within an auscultatory gap, should it exist. In order to avoid the auscultatory gap, a minimum number of pulses beyond the tallest pulses in the train (say beyond PMID2) is desired. Also, for accuracy there should be a minimum number, desirably sixteen, pulses in the pulse train. By using a bleed rate of 3-6 mm of $H_g$ per beat, this minimum number will usually be obtained. Thus, by implementing the instrument in a manner to obtain the minimum, proper operation by the operator is dictated.

The static cuff pressure (viz, the pressure as shown in FIG. 7) which is present at the same time as the pulses denoting the systolic and diastolic events is read as the systolic and diastolic blood pressures. In the event that the systolic pressure is not greater than the sum of the diastolic pressure and ten millimeters of mercury, an error is also indicated.

As noted above, the location of the diastolic and the systolic events in accordance with the proportional relationship which pulses in the train bear to the peak reference level, has been determined to be accurate by clinical data. This proportional or percent of peak relationship affords means for the automatic measurement of blood pressure with the same measurement accuracy as conventional, manual, sphygmomanometric techniques. The percent of peak method may readily be practised with the aid of a programmed data processor such as the microcomputer system described above. The microcomputer has means for selecting the peak average and the pulses in the sets which are at or below the systolic and diastolic thresholds. The processor has storage for digital signals representing values of the pulses in the peak table, the pulses in the pulse table, and the cuff pressures which are present at the same time as these pulses. The processor has means for computing the diastolic and systolic pressures from these digital signals as well as for recognizing artifacts and other sources of error. An exemplary program which is carried out by the apparatus in obtaining the blood pressure measurement is given by way of example in the flow charts of FIG. 6. These flow charts represent a program which can be performed with the instruction set of the microprocessor of a microcomputer such as uses the MCS 6503, MCS 6530, and other devices mentioned above, or through the use of other available microprocessors and associated devices.

Figure 6A:
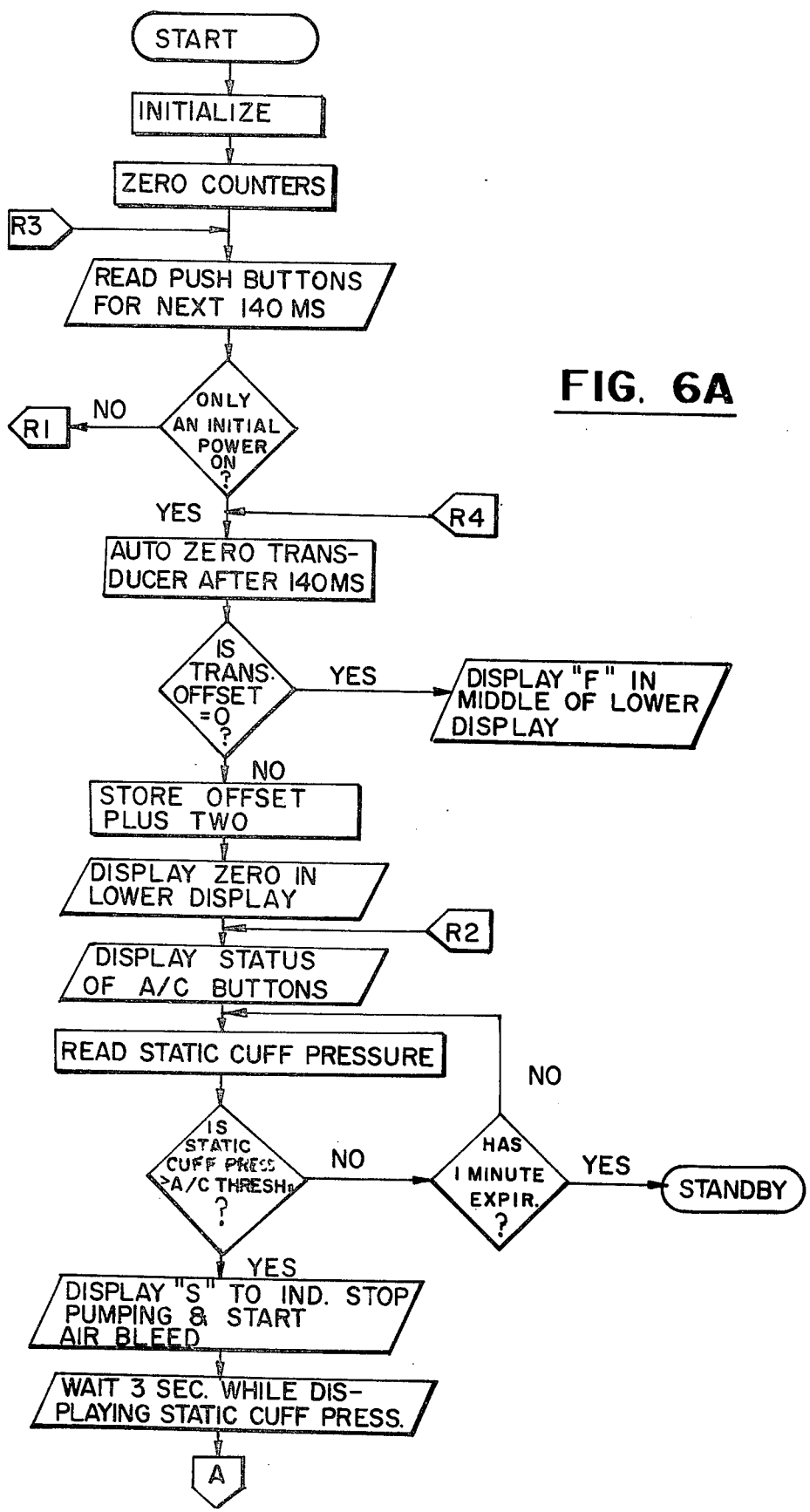
Figure 6B:
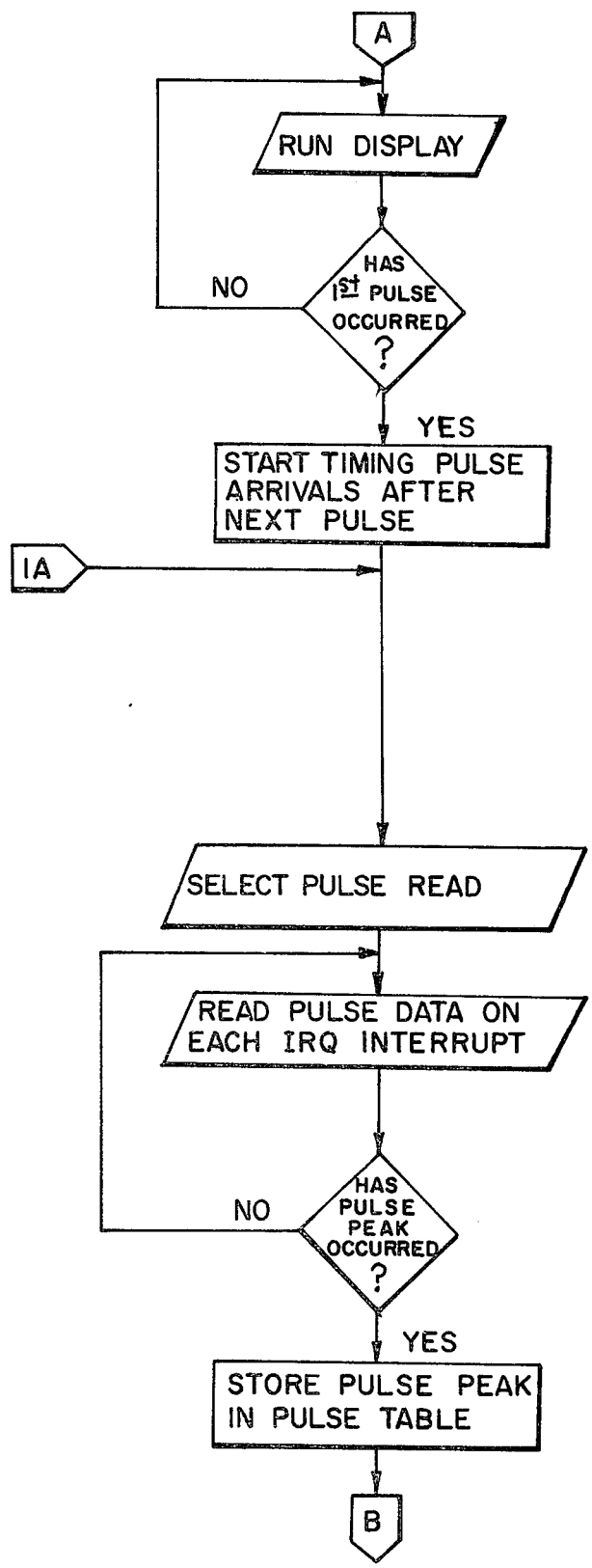
Figure 6C:
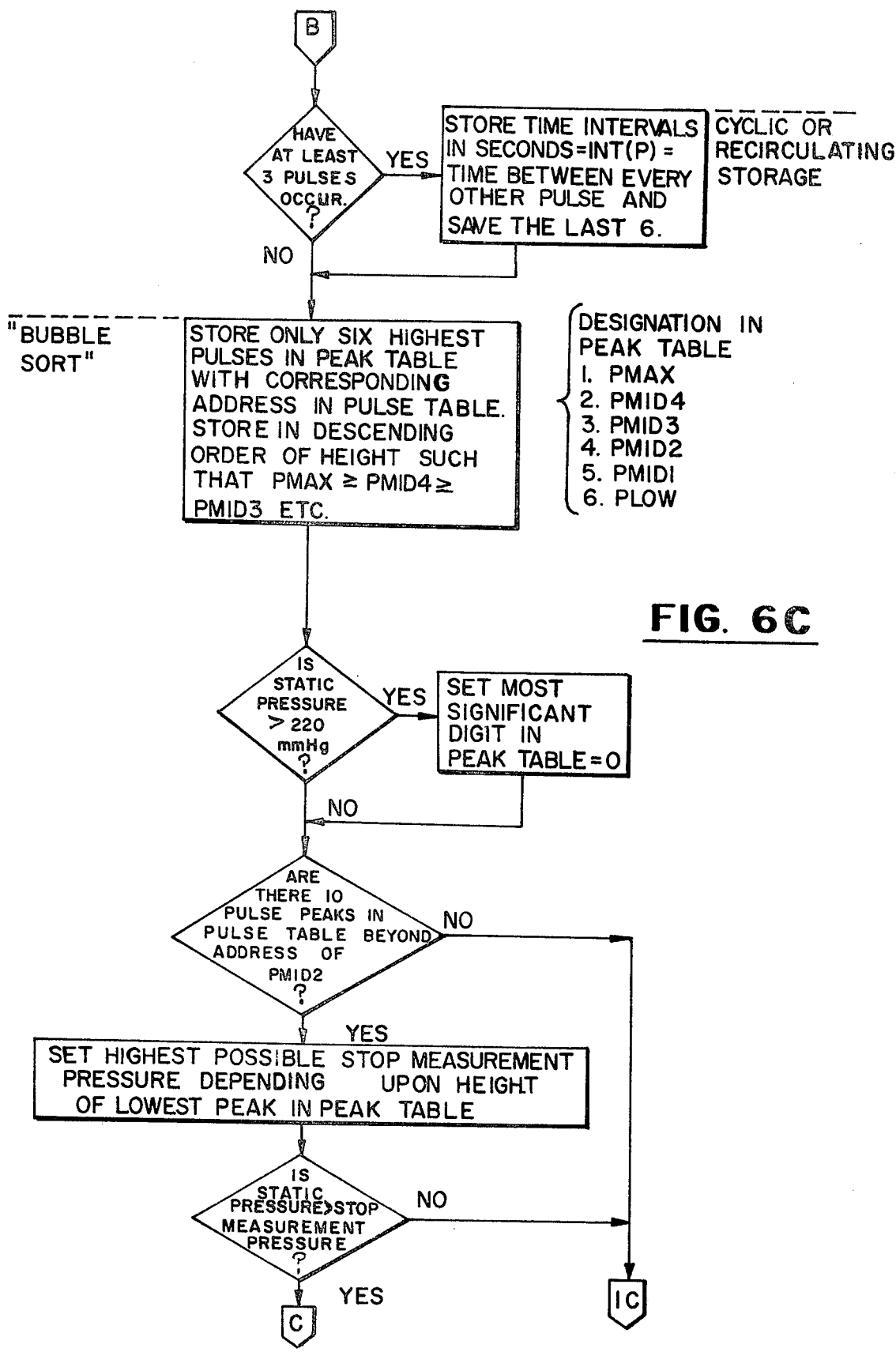

Referring to FIG. 6 and particularly to FIG. 6A, it will be noted that conventional flow chart symbols are used. A rectangle indicates an operation, a diamond represents a two-way decision, an oval connotes the start or end of a program, a five-sided polygon indicates a flow connector to another part of the program, and a parallelepiped denotes an input or output function.

The flow charts shown in FIGS. 6A through 6H show the general sequencing of the apparatus described in connection with FIGS. 1 through 5. The entry point for the entire apparatus which starts the sequence of events occurs when the ON button is pushed to turn on the power supply. A reset command RST is then generated by the comparator 68 and an inverter 70 (see FIG. 2) as $V_{R3}$ appears. This reset command initializes or zero's the counters in the CPU 82 and I/O port 84 of the microcomputer 40. It also initializes addresses in RAM to store certain data and also zeros addresses which serve in error counting. The push button controls 34 and 38 are read each conversion cycle for the next 140 m. sec. (milliseconds). At the end of a conversion cycle the $\overline{\text{AEOC}}$ command results in an $\overline{\text{IRQ}}$ which causes the entry of the push-button command data into the microcomputer.

If only the ON/OFF push button is ON, which denotes that only the power is on to the system, an autozero operation occurs after an interval of another 140 m.sec. This reads the transducer output (through the analog to digital converter 26). Inasmuch as the cuff is not inflated, zero pressure is assumed to be in the cuff. The cuff pressure is stored and this value is taken as the offset. If this offset is zero then a special error code ("F" in the middle digit of the lower display) is generated on the display to indicate transducer failure. The offset plus an added two units (2 mm of Hg) is then stored as the zero presure offset which is subtracted from each static pressure transducer output. The display will now not flicker in the lowest order digit. If the result of this subtraction is negative, then the term "static cuff pressure" used in the flow chart and description herein is set equal to zero otherwise the subtracted result is positive and is used directly for the cuff pressure in the program and display.

Figure 6D:
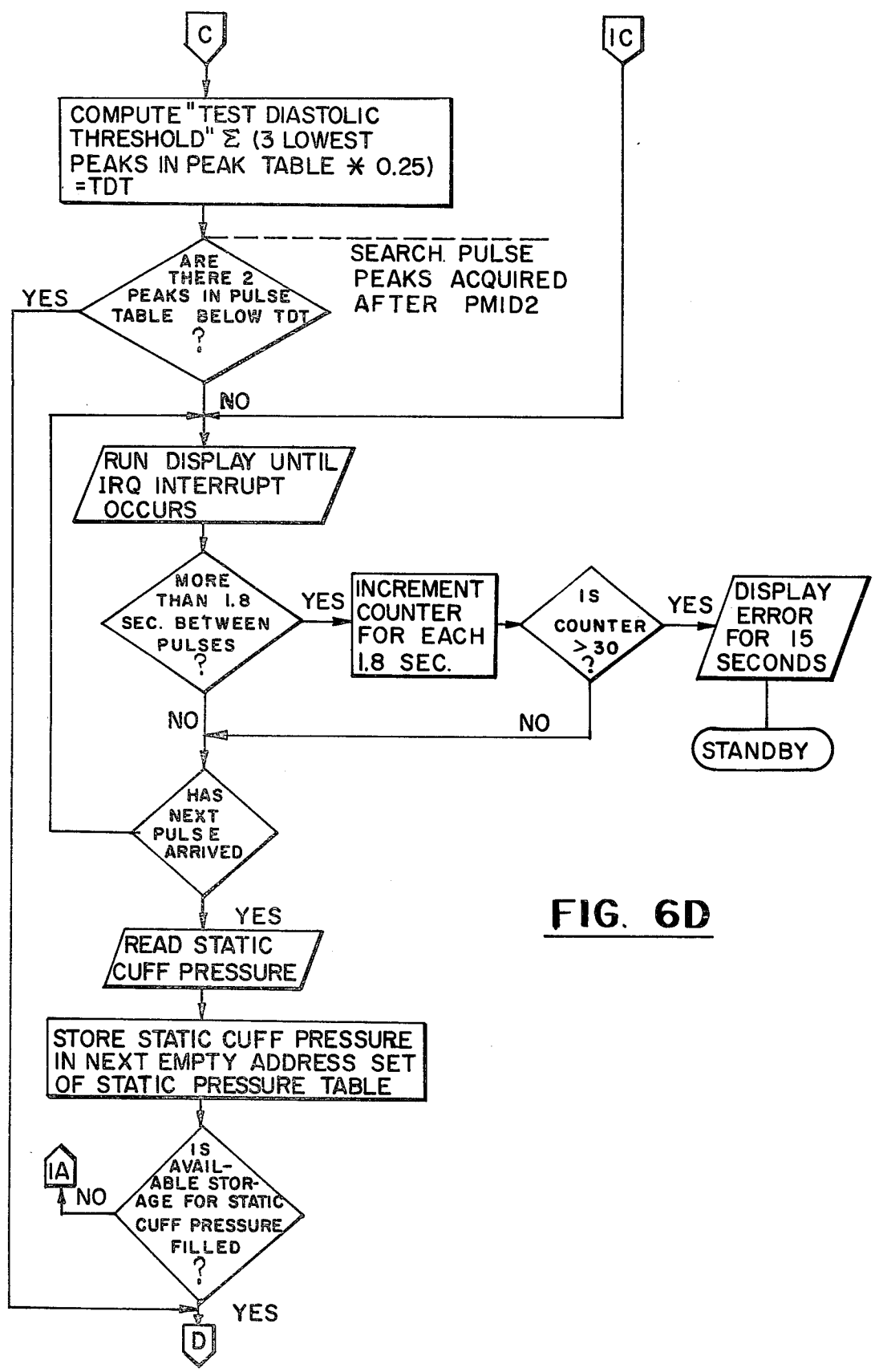
Figure 6E:
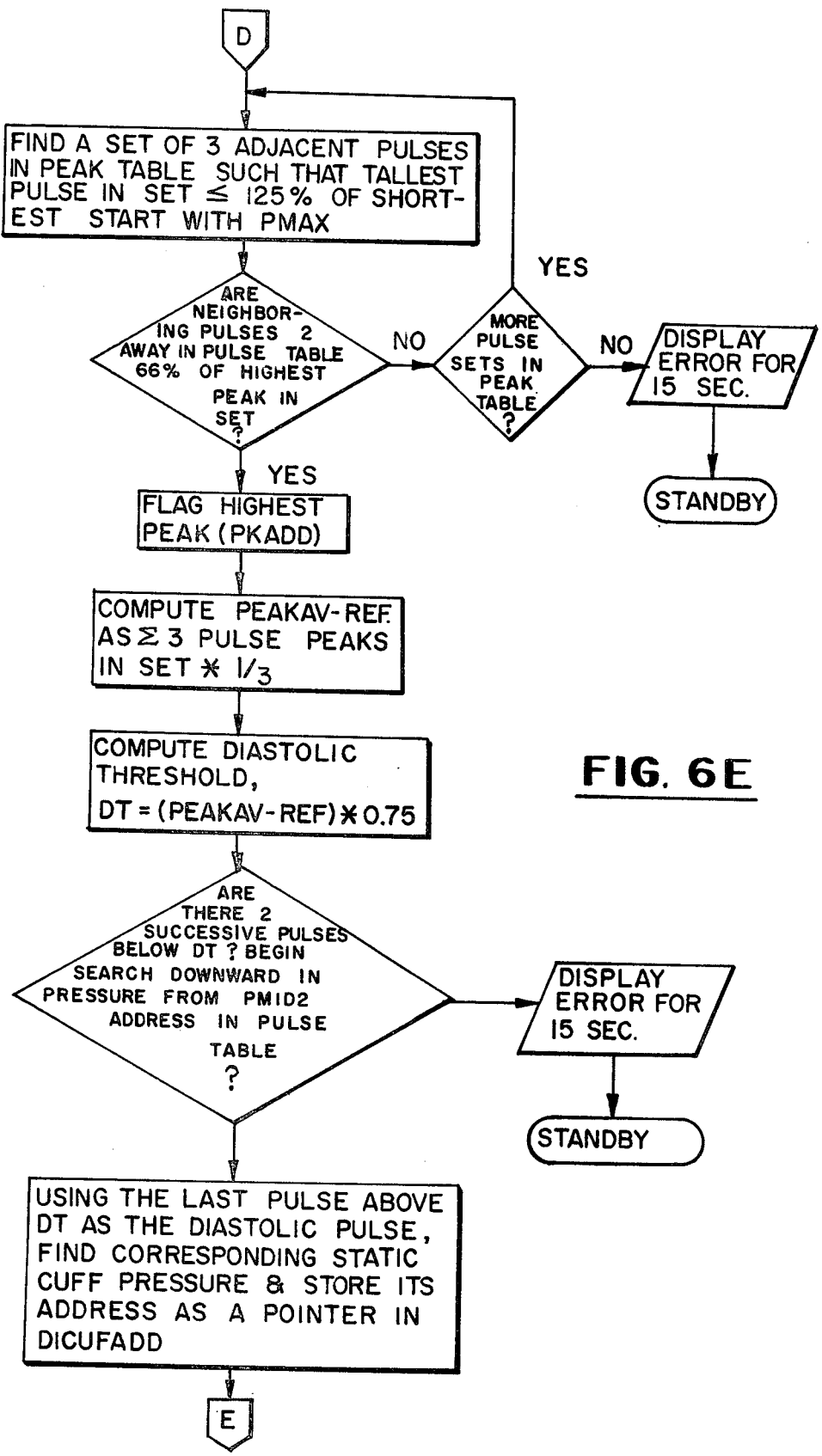
Figure 6F:
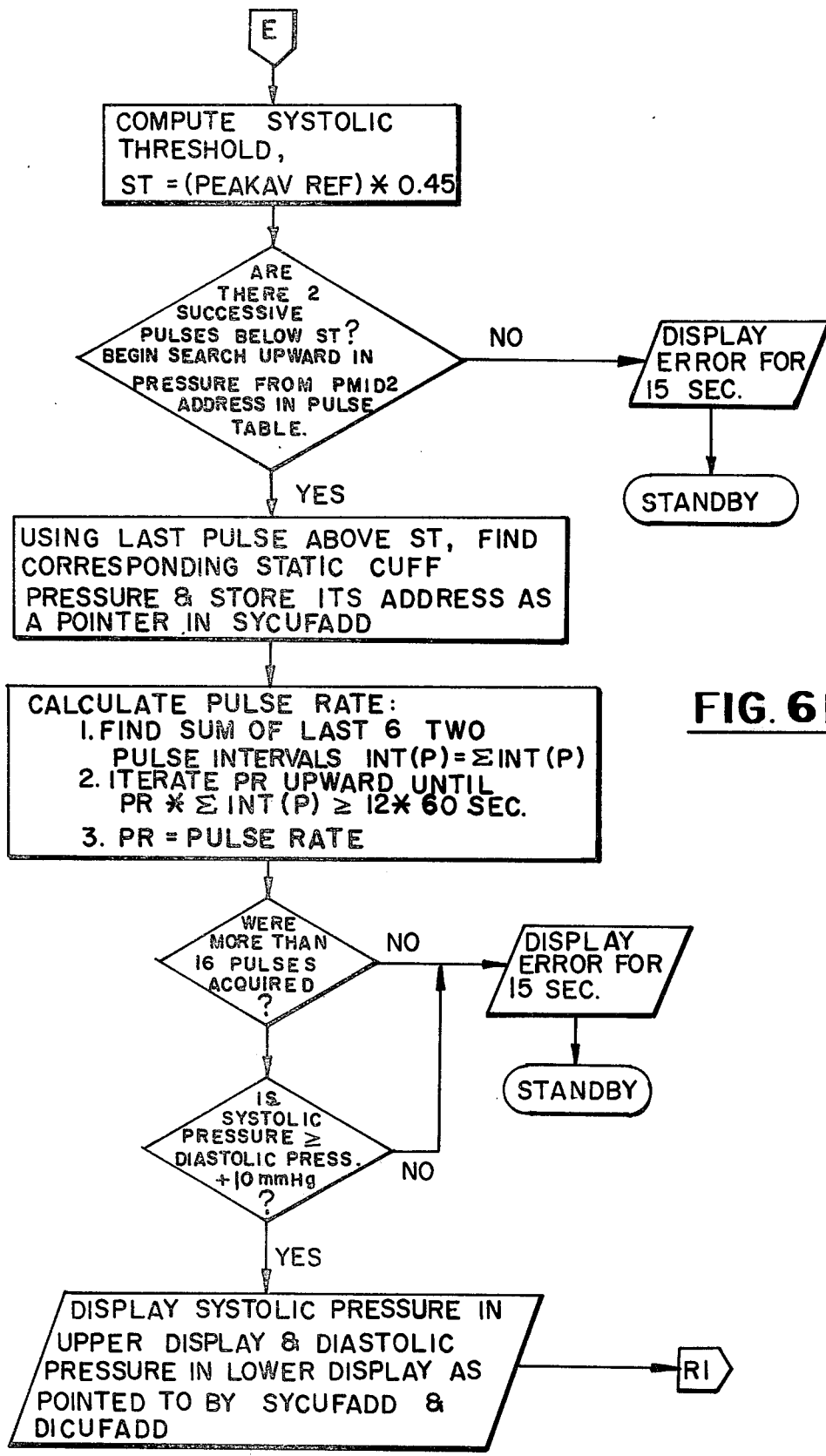
Figure 6G:
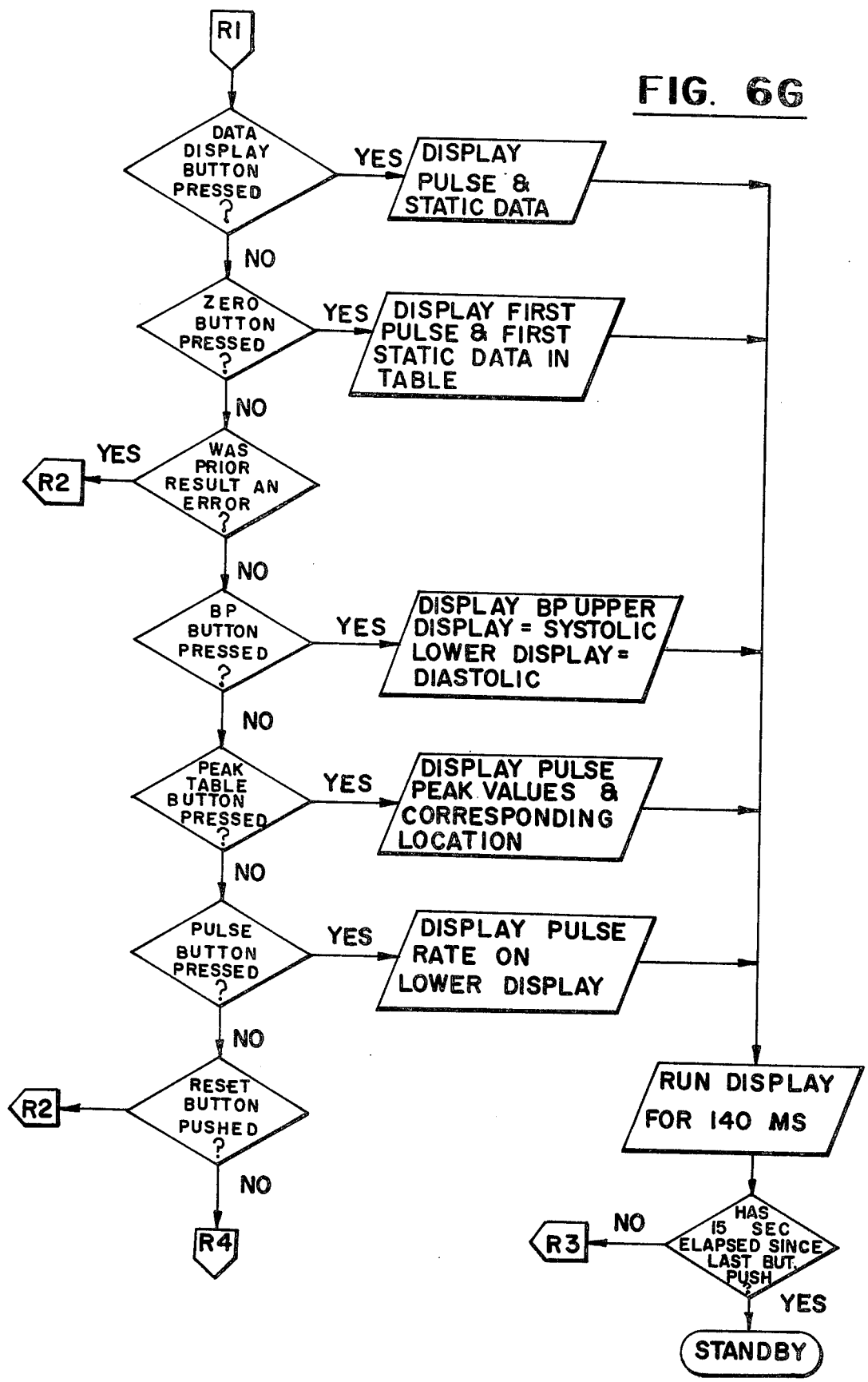
Figure 6H:
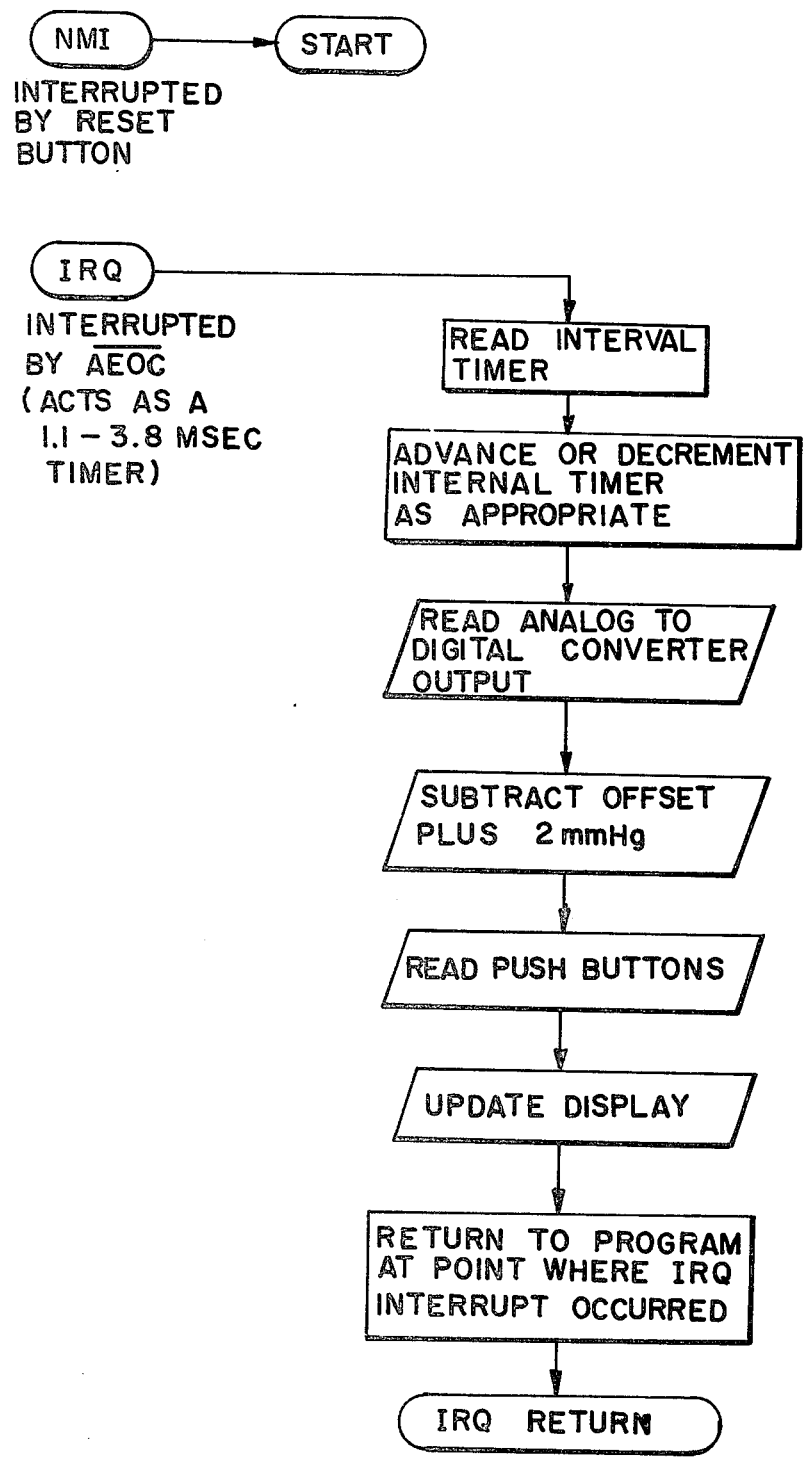

The "Reset" button has a special function in the instrument which is to activate the non-maskable interrupt (NMI) as shown in FIG. 6H. NMI always sends the program to the start position in the flow chart and is the only power "ON" exit from error. Since the "Reset" button is the last button checked as shown in FIG. 6G, if any other button of FIG. 6G has been pressed, then the latter button function will be activated in the program. This is useful as a diagnostic tool particularly with the data display button, since holding this button down during the NMI period (i.e. depression of "Reset") will send the program into the mode where the complete RAM storage may be stepped through at any time during or after the measurement. This diagnostic is available however for maintenance purposes. It is implemented by the auxiliary control buttons 38 (FIG. 1).

In the decode sequence shown in FIG. 6G, each of the questions regarding a button depression or a prior error result is asked in the sequence shown. With the exception of the "Reset" button and prior error result, an affirmative response results in a display of the appropriate function as shown in FIG. 6G. The "Reset" button and "prior error result" both send the program back through R2—R2 to FIG. 6A for the reset sequence. This sequence begins with the display of the adult/child button. The CPU outputs a letter A or letter C in the second digit from the right of the upper row of the display 42.

In the normal sequence of events for each blood pressure measurement the operator will, after the power ON button is pressed for the first measurement or the reset push button has been pressed for any subsequent measurement, inflate the cuff as by pressing repeatedly on the bulb 14 which serves as the pump (see FIG. 1). The pressure will rise until the static cuff pressure exceeds the applicable threshold, whether adult or child. This is accomplished by comparing the static cuff pressure as it is read into the computer on each conversion cycle during the inflation of the cuff with the threshold which is selected by pushing the adult/child button. If the threshold is not exceeded within one minute after the status of the adult/child button is displayed, it is assumed that the operator has left his or her post or the measurement has otherwise been aborted. The system would then proceed to the standby mode. When the adult/child threshold is exceeded, data output is to the display 42 to display the letter S (which is similar to the numeral 5) in the second digit from the right on the top row of the display. The operator then opens the valve 16 so that air starts to bleed out of the cuff. The time interval of three seconds is automatically interposed by the interval timer in the I/O port 84 during which the static cuff pressure is displayed. The operator is enabled to observe the gradual decrease in the static blood pressure during these three seconds and will recognize that the bleed rate is within the proper range, which may suitably be three to six mm of Hg per second.

The program then proceeds to acquire the data for the blood pressure and pulse rate measurement.

The subroutine used to input data (called ADTIME and DATACQ in the listing provided hereinafter) is shown in FIG. 6H.

An IRQ interrupt occurs at the end of each conversion cycle of the ADC 26. The IRQ results from the $\overline{\text{AEOC}}$ command. Inasmuch as the conversion cycle of the ADC may vary from 1.1 to 3.8 m.sec. depending upon the amplitude of the analog signal input, the $\overline{\text{AEOC}}$ commands appear each 1.1 to 3.8 m.sec. which can be considered as a 1.1 to 3.8 m.sec. timer.

The interval timer in the I/O port 84 (FIG. 4) is read to keep track of the elapsed run time of the program. The internal interval timers which are represented by data at different addresses in RAM 88 are also advanced or decremented again to track timing in the program.

Next the ADC 26 output is read into RAM via the CPU. Now the sum of the offset plus 2 mm of Hg is subtracted from the static pressure when static pressure is read from the ADC. No such subtraction takes place if the pulsatile pressure digital signal is outputted from the ADC 26. This provides the auto zero and flicker-free display as discussed above.

Next the push buttons are read with the pushbutton data in temporary storage in the RAM. On each interrupt the display is advanced to the next digit and that digit is updated. Thus each digit will be updated at least each 3.8 m.sec. which is sufficient to remove any flicker from the display. The program then returns to the initial point where the interrupt occurred (called an RTI instruction).

Cuff pressure data is continually acquired on each conversion cycle of the analog to digital converter 26 and held in temporary storage in the RAM 88 (FIG. 4). When the first pulse has occurred in the course of the measurement data acquisition routine (viz, the start of a new pulse) as indicated by the $\overline{\text{ASOP}}$ control signal, the interval of time between adjacent pulses is timed. The ASO signal is outputted to the switch 28 such that digital signals representing the amplitude of the pulse is outputted from the converter 26 (FIG. 2). Upon the next interrupt, IRQ, the cuff pressure digital signal and the corresponding pulse digital signal are read into memory in the RAM 88. The pulse digital signals which represent the values of each of the pulses are stored in the pulse table addresses or locations in memory. Corresponding cuff pressures are stored in the cuff table address locations.

The values of successive pulse digital signals are compared with each other. The comparison can be made between adjacent pulse signals while they are in temporary storage in the temporary storage registers of the CPU 82 (FIG. 4). When a pulse is detected which has an amplitude less than a preceding pulse the preceding pulse is identified as being a pulse peak. These pulse peaks are stored in consecutive addresses in the pulse table together with succeeding pulses and are "bubble sorted" into the peak table. For example, if a pulse is acquired which is higher than a pulse already in the table it will replace that pulse and the lower pulses will be displaced; and the lowest of these pulses will drop out of the table. After three of such pulse peaks are found, the pulse time separation for every other pulse in seconds for all succeeding pulses is acquired, but only the last six such intervals are stored as a quantity INT (P) (see FIG. 6C). These six pulse time intervals are stored in memory for use in computing the pulse rate. A cyclic or recirculating storage for such intervals is provided in RAM.

The six highest pulses in the pulse table at any point in the measurement and their addresses in the pulse table are stored separately in RAM 88 and constitute the peak table. The digital signals representing these pulse peaks are operated upon in the "bubble sort" routine, as discussed above, such that each new pulse peak with its address is re-arranged between two adjacent pulse peaks such that it is greater than or equal to the one below and less than the pulse above in the peak table. The excess pulse which is lower in amplitude than the lowest pulse is deleted such that there are six pulses in the peak table, the highest amplitude of which is designated as PMAX, the next as PMID4, the next as PMID3, the next as PMID2, the fifth lowest amplitude pulse as PMID1, and the lowest amplitude pulse as PLOW. There are now three tables in memory. The peak table, the pulse table, and the cuff static pressure table. Each of these tables is constituted of digital signals, each of which is stored as two or three 8 bit bytes in RAM 88 (FIG. 4).

In order to get rid of early artifacts, which can occur if the pulses in the peak table were acquired while the static cuff pressure was still high, the peak table is kept zeroed while the static pressure exceeds 220 mm of Hg.

The accuracy of the measurement depends upon there being sufficient data in the pulse table. The pulse table is therefore then checked for at least ten digital signals corresponding to pulse amplitudes in the pulse table beyond (in a direction of lower cuff pressures—which occur later in time when the deflation or bleed cycle occurs as is the case in this exemplary embodiment) the peak in the pulse table corresponding to PMID2 in the peak table. PMID2 is selected in that it is approximately in the middle of the peak table. If ten pulses are not located in the peak table beyond the address of PMID2 then the program jumps (see page connectors 1C-1C) to a routine shown in FIG. 6D for adding additional data to the cuff and pulse tables. This provides further assurance that pulses will be acquired after the occurrence of any auscultatory gap.

In the event that there are at least ten pulse peaks in the pulse table beyond the address of PMID2, an additional check is conducted upon the data which was acquired and stored to assure that such data is sufficient to assure a high degree of accuracy in the blood pressure measurement. To this end a stop measurement pressure is obtained based upon the height (the amplitude) of the lowest peak (PLOW) in the peak table. For example, if PLOW is a digital signal which is equal or less than 400 in decimal code, then the stop measurement pressure is set at 75 mm Hg. If PLOW is greater than 400 but less than or equal to 600 in decimal code, the stop measurement cuff pressure is set at 85 mm Hg. For PLOW values greater than 600 (decimal) the stop measurement cuff pressure is set at 120 mm Hg. These decimal values are related to the strength of the pulse (i.e., the output voltage from the pulsatile channel 24, FIG. 2). Thus more pulses will be acquired when the pulse is weak. This further assures accuracy.

The last aquired digital signal in the cuff table is then compared against the applicable stop measurement cuff pressure. If that cuff pressure is greater than the applicable stop measurement pressure, the program jumps to the routine for acquiring additional digital signals for the cuff and pulse tables.

If the cuff pressure is below the stop measurement pressure, the program proceeds via page connectors C-C and a "test diastolic threshold" (TDT) in terms of the product of the sum of the three lowest peaks in the peak table (PLOW, PMID1, and PMID2) and 0.25 (see FIG. 6D). This computation provides a worst case peak average reference from the three lowest peaks in the table rather than the three highest peaks. This again assures accuracy in the final measurement, which makes use of the three highest peaks, since it provides a further check that there will be sufficient data required and stored out of which highly accurate blood pressure measurements may be obtained. It will be observed that the TDT is a threshold less than or equal to any final diastolic threshold that may be found at this point in the course of data acquisition. The acquisition of at least the minimum number of pules for accurate location of the diastolic event is therefore dictated by the use of the TDT.

Each of the pulses in the pulse table acquired after the pulse which corresponds to PMID2, is examined. By "after" is meant located beyond the pulse table address of PMID2. If there are two digital signals in the pulse table having values which are below the value of TDT, the program jumps via page connectors D-D and proceeds with the routine for obtaining the systolic and diastolic blood pressures. However, when there is insufficient data in the pulse table out of which a blood pressure measurement of high accuracy may be obtained, the program proceeds through the routine for storing and acquiring additional data. Then new data from the analog to digital converter 26 (FIG. 2) is inputted to the microcomputer which runs the display 42 so that each new cuff pressure which is acquired is indicated. When an $\overline{ASOP}$ signal has arrived its occurrence is timed. The occurrence of ASOP connotes the occurrence of a pulse. If the next pulse, as denoted by the next ASOP signal which is detected is less than 1.8 seconds later, the new static cuff pressure digital signal and its corresponding pulse digital signal is read from temporary storage into the next empty address locations in the static cuff pressure table and the pulse table, respectively. If however more than 1.8 seconds elapses between pulses, (i.e. between ASOP's), a counter in the RAM 88 is incremented. When the count exceeds 30 (i.e., 54 seconds have elapsed) an error code is outputted to digit two (the second digit in the lower row of the display 42) for 15 seconds before going to standby mode. The only exit from this measurement error is via "reset" or "power off". This is in accordance with a feature of the invention which is to display an error signal rather than erroneous results and call for a new measurement.

Returning to FIG. 6D, another check for sufficient data for accuracy in the measurement is made by examining the last available address for static cuff pressures in RAM. If this address is filled, the program proceeds with the measurement routine via page connectors D-D. Otherwise the program jumps to FIG. 6B via page connectors 1A-1A so that the entire data acquisition routine is repeated. If the cuff has by then deflated to a point where further pulses are not detected, there will of course be more than 1.8 seconds between pulses and 54 seconds will expire such that an error indication will be displayed as indicated in FIG. 6D.

Next, the pulses are obtained which form the set from which the peak average reference can be obtained. Starting with the digital signal for PMAX, three adjacent signals (viz, the first test is for PMAX, PMID4 and PMID3) are compared and the set is selected if the tallest pulse (PMAX) is equal or less than 125% of the shortest. If PMAX does not satisfy this criteria, the next set of three adjacent pulses (PMID4, PMID3, and PMID2) are compared, and so forth until a set which satisfies the criteris is found. If no such set is found, the error indication is displayed as discussed above for other measurement errors.

In order to further assure that the set out of which the peak average reference is to be determined does not contain any artifacts, the digital signal in the pulse table corresponding to the tallest pulse in the set is compared with the pulses in the pulse table next adjacent thereto (i.e., neighboring pulses two away on both sides). If these next adjacent pulses are not equal or greater than 66% of the tallest pulse, the program jumps back to the routine of finding the set of three adjacent pulses in the peak table which satisfy the equal or greater than 125% criteria. The absence of any more sets of three pulses in the pulse table results in a command to display the error signal as discussed above for other measurement errors. If both tests for artifacts (the 125% and the 66% tests) are satisfied, the tallest peak (at PEAK-ADD) is flagged and kept so as to mark the peak average set. From this marked set the peak average reference, PEAKAV-REF is computed in terms of the product of the amplitudes (the pulse peaks) represented by the digital signals in the set and a factor of one third. From this PEAKAV-REF quantity the diastolic threshold, DT, is computed as the product of PEAKAV-REF and 0.75. This affords a diastolic threshold which has been determined empirically as being the exact diastolic threshold.

Next, the pulse in the pulse table which occurred at the time of the diastolic event is obtained. The digital signals in the pulse tables are examined searching downward towards lower cuff pressure from the pulse corresponding to PMID2 until two successive pulses are found which have amplitudes below the diastolic threshold DT. If no such pulses are found when the end of the pulse table is reached, an error is displayed and the system is readied for another measurement attempt.

The address of the pulse in the pulse table which last had an amplitude higher than the diastolic threshold is then flagged as the diastolic event indicating pulse. It will be observed therefore that a set of three adjacent pulses are located in the pulse table, the first of which is above and the last two of which are below the diastolic threshold. The first pulse is then taken as the diastolic pulse. The corresponding static cuff pressure (viz, the static cuff pressure in the static cuff table which was acquired by successive interrupts, IRQ) is flagged and its address is used as a pointer (the address being called DICUFADD). When the blood pressure button has been pressed, this address will be called up and will point to the cuff pressure digital signal in the cuff table such that this cuff pressure digital signal will be read out to the display and displayed in the lower display as the diastolic pressure (see FIG. 6G). A display of diastolic pressure and systolic pressure will automatically occur even if the blood pressure button is not pressed after the systolic pressure is obtained (see FIG. 6F—last block thereof).

The systolic pressure measurement is obtained as the program proceeds via page connectors E-E. The systolic threshold (ST) is computed as the product of the PEAKAV-REF and 0.45. This obtains the empirically derived systolic threshold as was explained above in connection with FIG. 8.

The pulse table is then searched beginning from the pulse corresdponding to PMID2 in the peak table in an upward direction, i.e., towards higher cuff pressures. If there are no two successive pulses of amplitude below the systolic threshold the measurement error indication is displayed as shown in FIG. 6E. If there are two successive pulses, the pulse adjacent to the first of these two successive pulses which has an amplitude higher than the systolic threshold is flagged and the address of this pulse (called SYCUFADD) is used as a pointer for readout of the static cuff pressure in the cuff pressure tables which correspond thereto. In other words, the pulse which is above ST is the first pulse of a set of consecutive pulses one of which is equal to as at ST and the others of which are below ST. This set is located in the pulse table before the pulse corresponding to PMID2 in the peak table. The systolic pulse and the cuff pressure corresponding thereto were acquired upon occurrence of successive interrupt (IRQ) commands.

The systolic pressure which has been obtained will be displayed unless two other criteria which indicate whether or not a proper blood pressure measurement has been obtained are satisfied. These criteria are (a) whether more than 16 pulses have been acquired, and (b) whether the systolic pressure is equal or greater than the sum of the diastolic pressure and 10 mm Hg. Unless these criteria are satisfied, the system is operative to indicate an error measurement on the display as shown in FIG. 6F.

Prior to the test for the 16 pulses and the systolic pressure magnitude, the system is operative to calculate the pulse rate. When the pulse table was acquired (see FIG. 6C) six time intervals, INT(P) were stored. The pulse rate is calculated in terms of the sum of these six INT(P) intervals. The average of these intervals is obtained and the units are converted into seconds by finding a value, PR, which when multiplied by the sum of the INT(P) interval, is equal or greater than 720. PR is stored in memory and is read out when the pulse button is pressed (see FIG. 6G).

The system is operative to read out blood pressure, pulse rate or any of the auxiliary data items when the push buttons for such data are pressed. The display alone runs for 140 ms after a button is pressed. The display also runs for another 140 ms (see connectors R3-R3 to FIG. 6A). Thus the data, whether blood pressure, pulse rate or other data, will be displayed for a sufficient length of time to be observed by the operator of the system. Of course, the display may be a printer which will provide hard copy if desired, and sufficient time for display will be allowed so as to complete the print out. If another button is pressed the display command by that button is read for another 280 ms.

The interval timer in the I/O port 84 (FIG. 4) is started each time a push button is pressed. If fifteen seconds has elapsed, the system switches to standby and will remain in the standby mode until the ON/OFF button is pressed to OFF. Of course full power returns, if prior to the end of the fifteen seconds period, the system measurement is recalled, as will occur if any of the other buttons are pushed (FIG. 6G connecting to FIG. 6A via page connectors R3-R3). If the reset button is pushed the program jumps via R2-R2 back to FIG. 6A for the next measurement.

By way of illustration the listing of the program shown in FIG. 6 which may be used for the MOS technology microcomputer as discussed in connection with FIGS. 1 through 5 is presented below: The subroutines: BCDMULT; BCDCOMP; BCDCOMPT; BCDCOMP1; PROCESS 1; ADTIME; DATACQ; LOWBATT; DISPLAY; PRESTOR; WAITDATA; CLKFLG1; ERRORINC; ERROR; DIMCMPY; PKSRCH8; FINISH1B; AND FINTIME are located at the beginning of the listing. Other subroutines ADDCHK AND STANDBY are located at the end of the listing.

The instructions and address modes (e.g., IM for immediate, ZP for zero page in RAM, ZPX for zero page in RAM indexed on X register, ZPY zero page index on X register, and etc), which are listed are those in the MOS technology instruction set for the MCS 6503 microprocessor, except that CLRD is the same as CLR in the MOS technology set; similarly CLRC is the same as CLC; CLRI is the same as CLI; CLRV is the same as CLV; BNEQ is the same as BNE; and NOPP is the same as NOP. The address modes are also the same in the listing as in the MOS technology set except IY means (IND), Y in the MOS technology set and IX means (IND,X) in the MOS technology set. Also Y means ABS, Y and X means ABS, X in the MOS technology set. Other minor differences will be apparent.

The zero and page 1 addresses in RAM for the memories used in the listing and the description thereof are set forth immediately after the listing as TABLES IA to IE.

It will be appreciated, of course that the invention is not limited to any particular listing since the listing will depend upon the architecture of the microcomputer or other data processor which is used.

```
* SUBROUTINE BCDMULT
*         ENTRY POINT FOR BCD MULTIPLICATION IS BCDMULT
*         ENTRY POINT OF BINARY MULTIPLIER IS BINMULT
*         (OP1ADDL) POINTS AT MULTIPLICAND WHICH IS MOVED TO
*         MCANDTMP,ZP (4DIGIT FIELD)
*         (OP2ADDL) POINTS AT MULTIPLIER FIELD (2 BYTE, 4 BCD DIGITS)
*         RESULT OF MULTIPLICATION IS LEFT IN PRODUCT,ZP; RIGHT JUSTIFI
*         INTEGER FORM
BCDMULT   SED
BINMULT   LDX    3,IM,HD
          STX    DIGCNT,ZP       INITIALIZE MULTIPLIER LENGTH COUNTER
          LDA    0,IM,HD
BCDMULT1  STA    PRODUCT,ZPX     ZERO PRODUCT FIELD
          STA    MCANDTMP,ZPX    ZERO MULTIPLICAND FIELD
          DEX
          BPL    BCDMULT1        LOOP UNTIL FINISHED
          LDY    1,IM,HD
BCDMULT2  LDA    OP1ADDL,IY      GET MULTIPLICAND DIGIT INDIRECT
          STA    MCANDTMP+2,Y    STORE IN RIGHT NND OF MCANTMP
          DEY
          BPL    BCDMULT2
BCDMULT7  LDA    DIGCNT,ZP
          LSR    ,AC             PUT LSB IN CARRY (ODD,EVEN TEST)
          TAY
          LDA    OP2ADDL,IY      GET PROPER BYTE OF MULTIPLIER
          BCS    BCDMULT0        GO AROUND IF RIGHT HAND DIGIT
          LSR    ,AC
          LSR    ,AC
          LSR    ,AC
          LSR    ,AC             SHIFT LEFT DIGIT OBER
BCDMULT0  AND    0F,IM,HD        MASK RIGHT HAND DIGIT
          STA    MULTDIG,ZP
          BEQ    BCDMULT9        SEE IF MULTIPLIER DIGIT IS ZERO
BCDMULT3  LDX    3,IM,HD
          CLRC
BCDMULT4  LDA    MCANDTMP,ZPX    DECIMAL ADD MULTIPLICAND FIELD TO
          ADC    PRODUCT,ZPX           PRODUCT FIELD
          STA    PRODUCT,ZPX
          DEX
          BPL    BCDMULT4        GO FOR ALL DIGITS IN FIELD
          DEC    MULTDIG,ZP      DECREMENT MULTIPLIER DIGIT
          BNEQ   BCDMULT3        GO ADD FIELDS AGAIN UNTIL MULTDIG IS
BCDMULT9  DEC    DIGCNT,ZP       ARE WE OUT OF DIGITS?
          BMI    BCDMULT8        QUIT WHEN DIGCNT IS NEGATIVE
          LDY    4,IM,HD         PREPARE 4 BIT MULTIPLICAND SHIFT
BCDMULT5  LDX    3,IM,HD
          CLRC
BCDMULT6  ROL    MCANDTMP,ZPX    SHIFT LEFT
          DEX
          BPL    BCDMULT6        GO OVER 4 BYTES
          DEY
          BNEQ   BCDMULT5        SHIFT 4 BYTES 4 TIMES TO THE LEFT
          BEQ    BCDMULT7        ALWAYS BRANCH
BCDMULT8  CLRD
          RTS
* SUBROUTINE BCDCOMP - COMPARE DATA IN OLDDATA WITH THAT IN NEWDATA
*         ON EXIT C=0 IF OLDDATA>NEWDATA, C=1 IF OLDATA<NEWDATA OR=
BCDCOMP   SED
          SEC
```

```
            LDA       NEWDATA+1,ZP
            SBC       OLDDATA+1,ZP    DECIMAL SUBTRACT LSD'S
            LDA       NEWDATA,ZP      DON'T RE STORE
            SBC       OLDDATA,ZP      SUBTRACT MSD'S
            CLRD
            RTS
* SUBROUTINE BCDCOMPT                 COMPARE USING ADDRESSES IN X AND Y R
*           C=1 IF (X)<(Y); C=0 IF (X)>(Y)
*           X HAS ZP ADD. OF LEFT BYTE OF DATA FIELD
*           Y HAS LSB OF ADDD. OF LEFT BYTE OF OTHER DATA FIELD (ZP)
BCDCOMPT    SED
            SEC
            LDA       1,Y             GET LSBYTE POINTED AT BY Y
            SBC       1,ZPX           SUB. DEC. FIELD POINTED AT BY X
            LDA       0,Y             GET MSBYTE
            SBC       0,ZPX
            CLRD
            RTS
* SUBROUTINE BCDCOMP1 - COMPARE DATA ON PAGE 1 (Y), WITH ZPX
BCDCOMP1    SED
            SEC
            LDA       257,Y
            SBC       1,ZPX
            LDA       256,Y
            SBC       0,ZPX
            CLRD
            RTS
* SUBROUTINE PROCESS1 DO SOME ADDING AND MULTIPLYING
PROCESS1    LDA       0,IM,HO         ZERO OUT PEAKAV
            STA       PEAKAV,ZP
            STA       PEAKAV+1,ZP
PROCESS2    CLRC
            SED
            LDA       1,ZPX
            ADC       PEAKAV+1,ZP
            STA       PEAKAV+1,ZP
            LDA       0,ZPX
            ADC       PEAKAV,ZP
            STA       PEAKAV,ZP
            CLRD
*           ---- END OF ADDITION OF FIELDS
            DEX
            DEX
            DEX
            DEY
            BPL       PROCESS2        ADD THREE SUCCESSSIVE FIELDS
            LDA       PEAKAV,IM,SAL
            STA       OP1ADDL,ZP
            JSR       BCDMULT         FIND DIASTOLIC LEVEL
            LDX       PKADD,ZP
            LDY       2,ZPX           GET ADDRESS AT LOCATION 2 PAST (PKAD
            LDX       PRODUCT+1,IM,SAL
            RTS
* IRQ SUBROUTINE ADTIME
*           PC AND P ARE SAVED BY INTERRUPT
*           RETURN WITH NEW DATA AND STATUS
ADTIME      PHA                       SAVE ACC.
            TXA       SAVE X
            PHA
            TYA
            PHA                       SAVE Y
            CLRD
* RESTART TIMER
            LDX       7F,IM,HO        SET TIMER TO 7F HEX
            TXA
            SEC
            SBC       TIMREAD,AB      SUBTRACT CURRENT VALUE OF TIMER
            STX       TIMBASWD+2,AB   RUN TIMER- 80 D 64T WOIRQ/PB7
            CLRC
* UPDATE CLOCK
            ADC       TIMINTCY+1,ZP   ADD IN LSBYTE OF TIMER CYCLE CLOCK
            STA       TIMINTCY+1,ZP   STORE BACK
            BCC       ADTIME1         GO AROUND IF NO CARRY
            INC       MINCLK1+1,ZP
            BNEQ      ADTIME10        GO AROUND
            INC       MINCLK1,ZP      MSBYTE OF MINCLK1
ADTIME10    DEC       TIMINTCY,ZP     RUN TIMINTCY BACKWARDS
            BNEQ      ADTIME1         GO ON IF MSBYTE OF TIM. NOT ZERO
            LDA       36,IM,DD        RESTORE TIMINTCY TO 36 DEC IF ZERO
            STA       TIMINICY,ZP
* CYCLE CLOCK
*                                     0.01 MINUTE CLOCK
            DEC       MINCLOCK,ZP     COUNT DOWN MINCLOCK - BINARY
            LDA       PLSFLG,ZP
            BNEQ      ADTIME1         GO AROUND IF PULSE TIMER IS DISSABLE
            DEC       PLSWAIT,ZP      RUN PLSWAIT CLOCK
            BPL       ADTIME1         GO AROUND IF IT HASN'T TIMED OUT YET
            JSR       ERRORINC        INC ERRORCOUNTER IF WE HAVE GO TOO L
* SUBROUTINE DATACQ    RUNS A/D CONVERTER
*           CUFPLS =0 FOR READ PULSE, =1 FOR READ CUFF PRESSURE ON ENTRY
*           ENTERED FROM IRQ SERVICE ROUTINE
```

```
*       ACQUIRED DATA IS IN DATINTMP,ZP WITH MSD IN LOW BYTE
*       IF MSD IS NEGATIVE, OVERFLOW OCCURRED ON A/D CONVERSION
*       DATA ACQUIRED IS FROM CUFF/PULSE SOURCE SELECTED THE PREVIOUS
*         TIME THIS ROUTINE WAS ENTERED.
ADTIME1   LDA      DATAPAR,AB       SAVE PA REG.
          STA      DATAREG,ZP
          LDA      7,IM,HD
          STA      DATAPBDR,AB      SMAKE PB0,1,2 OUTPUTS, PB3-7 INPUTS
          LDX      CUFPLS,ZP
          STX      DATAPBR,AB       WRITE OUT CUFF/PULSE SELECT
          LDY      3,IM,HD          INITIALIZE LOOP COUNTER
          LDA      0,IM,HD
          STA      DATINTMP,ZP      ZERO MSD IN DATA AREA
          STA      DATAPADR,AB      SET UP PA AS INPUT
*------------ DATA ACQUISITION LOOP --------
DATACQ2   LDA      DATAPBR,AB       GET PB FOR EACH DIGIT N=4
          NOPP
          PHA
          LDA      DATAPAR,AB       GET PA
          PHA
          LDA      DATAPAR,AB       DUMMY LOOP EXTENDER
          DEY
          BNEQ     DATACQ2          TOTAL LOOP CYCLES IS 25 OR 26
          JSR      PRESTOR          RESTORE I/O REGS. TO DISPLAY
          LDY      3,IM,HD
*------------DATA FORMATTING LOOP ----------
DATACQ7   LDX      0,IM,HD
          PLA                       GET PA OF STACK
          PHA      SAVE A COPY
DATACQ4   INX                       LOOP TO FIND DIGIT NUMBER
          ASL      ,AC              X=1-D3,2-D2,3-D1
          BMI      DATACQ4          N=0 FOR DIGIT SELECT
          PLA
          PHA
          AND      0F,IM,HD         ISOLATE BCD DIGIT
          STA      DATINTMP,ZPX     STORE IN PROPER PLACE
          PLA                       GET PA AGAIN
          BMI      DATACQ6
          CPX      1,IM,HD
          BEQ      LOWBATT          X=1 AND BIT 7=0
DATACQ5   INC      DATINTMP,ZP      OVERFLOW OR D4 SET
DATACQ6   PLA                       GET PB FOR THIS DIGIT
          CLRC
          ROL      ,AC
          ROL      ,AC
          PHA
          LDA      40,IM,HD         SET BIT 6 OF PBSTAT
          ORA      PBSTAT-1,ZPX
          STA      PBSTAT-1,ZPX     ALLOWS NEW ZWERO TO BE DETECTED
          PLA
          AND      PBSTAT-1,ZPX     PICK UP ANY NEW PUSHBUTTONS
          STA      PBSTAT-1,ZPX     STORE IN PROPER BIN FOR LATER USE
          DEY
          BNEG     DATACQ7
*  ----------DATA PACKING LOOP -----------------
BCDPACK   LDX      3,IM,HD          INITIALIZE OFFSET IN DATINTMP
          LDY      1,IM,HD          INITIALIZE LOOP COUNT AND NEWDATA OF
BCDPACK1  LDA      DATINTMP,ZPX     GET UNPACKED BYTE
          STA      NEWDATA,Y        STORE TEMP. IN NEWDATA
          DEX
          LDA      DATINTMP,ZPX     GET ANOTHER UNPACKED BYTE
          ASL      ,AC
          ASL      ,AC
          ASL      ,AC
          ASL      ,AC              SHIFT OVER TO LEFT
          ORA      NEWDATA,Y        OR IN FIRST DIGIT
          STA      NEWDATA,Y        STORE BACK
          DEX
          DEY
          BPL      BCDPACK1         GO BACK AND GET OTHER DIGITS
          LDA      FCFLAG,ZP        ARE WE GETTING RESET DATA?
          BMI      OFFADJ2          BYPASS IF YES
          LDA      1,IM,HD
          CMP      CUFPLS,ZP        ARE WE GETTING CUFF DATA?
          BNEQ     OFFADJ2          BYPASS IF NO
          TAX
          SED
          SEC
OFFADJ1   LDA      NEWDATA,ZPX      DECIMAL SUBTRACT
          SBC      OFFSET,ZPX         2 BYTES
          STA      NEWDATA,ZPX        OF OFFSET
          DEX
          BPL      OFFADJ1
          CLRD
          BCS      OFFADJ2          IS OFFSET TOO BIG
          LDA      0,IM,HD
          STA      NEWDATA+1,ZP     ZERO IF NEGATIVE
          STA      NEWDATA,ZP
OFFADJ2   LDA      FF,IM,HD
          STA      FLAGCOM,ZP
          PLA
```

```
                TAY                             RESTORE Y
                PLA
                TAX                             RESTORE X
                PLA                             RESTORE ACC.
                RTI                             RETURN FROM INTERRUPT WITH INT. ENAB
* SUBROUTINE LOWBATT - DEAD END LOOP MONITORS LOWBATT SIGNAL
LOWBATT   LDA         0B,IM,HD                  SET 'b' IN LOWER DISPLAY
LOWBATT2  LDY         0,IM,HD                   SET OFFSET REG.
          STA         OP5ADDL,IY                STORE 'b'
          INY
          STY         DIGSEL,ZP                 SEL. DIG. 1
          JSR         DISPLAY                   GO DISPLAY
LOWBATT1  JMP         LOWBATT1                  INFINITE LOOP
* SUBROUTINE DISPLAY - DOES I/O TO DISPLAY REGS.
*         DATA FIELD POINTED AT BY OP4ADD IS PUT IN UPPER REG. IN DISPL
*         DATA FIELD POINTED AT BY OP5ADD IS PUT IN LOWER REG. IN DISPL
*         WILL SUPPRESS LEADING ZEROS
DISPLAY   JSR         PRESTOR                   RESTOR I/O REGS. TO DISPLAY
          LDA         DIGSEL,ZP                 GET DIGIT POINTER
          TAX
          CMP         4,IM,HD                   UPPER/LOWER DISPLAY
          BPL         DISPLAY2
*------------LOWER DISPLAY
          LSR         ,AC                       DIVIDE BY 2
          TAY
          LDA         OP5ADDL,IY                GET PROPER BYTE
          BCS         DISPLAY1                  RIGHT HAND DIGIT?
          LSR         ,AC
          LSR         ,AC
          LSR         ,AC
          LSR         ,AC                       SHIFT MSD BYTE OVER TO RIGHT END
DISPLAY1  AND         0F,IM,HD                  SET PA7 TO 0
          BNEQ        DISPLAY4                  IS DIGIT =0?
          CPX         1,IM,HD
          BEQ         DISPLAY5                  SEND DIGIT OUT WITH DIG SEL =0
          BNEQ        DISPLAY4                  ADD ON DIGIT SEL.
*------------ UPPER DISPLAY -------------
DISPLAY2  AND         3,IM,HD
          LSR         ,AC
          TAY
          LDA         OP4ADDL,IY                GET DATA BYTE FOR UPPER DISPLAY
          TAY
          BCS         DISPLAY3                  RIGHT HAND DIGIT?
          LSR         ,AC
          LSR         ,AC
          LSR         ,AC
          LSR         ,AC                       SHIFT MSD OVER TO RIGHT
DISPLAY3  AND         0F,IM,HD                  MASK OUT UPPER DIGIT
          BNEQ        DISPLAY4                  IS DIGIT=0
          CPX         4,IM,HD                   IS THIS DIGIT 4
          BEQ         DISPLAY5                  DIGIT SEL=0
          CPX         5,IM,HD                   IS THIS DIGIT 5
          BNEQ        DISPLAY4                  PUT ON DIGIT SEL. IF NO
          CPY         0,IM,HD                   IS DIGIT 4=0 ALSO?
          BEQ         DISPLAY5                  DIG. SEL. =0 IF YES
*------------ DIGIT SELECTOR ------------
DISPLAY4  CMP         0D,IM,HD                  IS DIGIT =0? BLANK SYMBOL
          BNEQ        DISPLAY6
DISPLAY5  LDX         0,IM,HD                   BLANK DISPLAYED DIGIT
DISPLAY6  STA         DISPWORK,ZP
          TXA
          ASL         ,AC                       SHIFT OVER DIGIT SELECTOR
          ASL         ,AC
          ASL         ,AC
          ASL         ,AC
          ORA         DISPWORK,ZP               ASSEMBLE DIGIT
          CPX         6,IM,HD
          BNEQ        DISPLAY7
          ORA         TEMPT,ZP                  TURN ON DECIMAL IF PROPER
DISPLAY7  STA         DATAPAR,AB                OUTPUT NEW DIGIT
          RTS                                   GO BACK
* SUBROUTINE PRESTOR
*         RESTORE PA0-7 AND PB0-2 AS OUTPUTS AND PB3-7 AS INPUTS
*         SET PB2=1 (DISPLAY MODE), RESTORE PROPER CUFPLS VALUE TO SELEC
*         RETURN PREVIOUS DISPLAY
PRESTOR   LDA         DATAREG,ZP
          STA         DATAPAR,AB
          LDA         CUFPLS,ZP
          ORA         04,IM,HD                  TURN ON PB2
          STA         DATAPBR,AB
          LDA         FF,IM,HD
          STA         DATAPADR,AB               MAKE PA OUTPUT
          LDA         7,IM,HD
          STA         DATAPBDR,AB               MAKE PB0-2 OUTPUT
          RTS
* SUBROUTINE WAITDATA
*         ACC. CONTAINS # OF CONV. CYCLES
WAITDATA  STA         DIGCNT,ZP                 SET UP INTERRUPT CYCLE LOOP COUNTER
```

```
WAITDAT1    LDA     FLAGCOM,ZP
            BPL     WAITDAT1
            DEC     DIGSEL,ZP
            BNE     WAITDAT2
            LDA     7,IM,HD
            STA     DIGSEL,ZP
WAITDAT2    INC     FLAGCOM,ZP
            JSR     DISPLAY         RUN DISPLAY
            DEC     DIGCNT,ZP
            BPL     WAITDAT1
            RTS
* SUBROUTINE CLKFLG1   ZEROS MINFLG1,MINCLK1
CLKFLG1     LDA     0,IM,HD
            STA     MINFLG1,ZP
            STA     MINCLK1,ZP
            STA     MINCLK1+1,ZP
            RTS
* SUBROUTINE ERRORINC
ERRORINC    INC     ERRORCNT,ZP
            LDA     ERRORCNT,ZP
            CMP     30,IM,DD
            BPL     ERROR           ERROR OUT AFTER 30 OVERTIMES
            LDA     NEWDATA,IM,SAL  IN CASE OF LONG DELAY
            STA     OPSADDL,ZP      POINT LOWER DISPLAY AT
            RTS                     CUFF PRESSURE
*-------FALL INTO ERROR ---------------
* SUBROUTINE ERROR
ERROR       LDA     0D,IM,HD        BLANK DISPLAY POSITION
*           ACC. CONTAINS ERROR # UPON ENTRY
ERROR4      ORA     E0,IM,HD        SET ERROR SYMBOL
            LDY     1,IM,HD         PREPARE TO STROE ERROR NO.
            STY     OPSADDL,ZP      MAKE LOWER DISP LOOK AT 0001 AND 000
            STY     PLSFLG,ZP       QUIT MONITORING PULSE PERIOD
ERROR1      STA     OPSADDL,IY
            LDA     0D,IM,HD        BLANK OUT EVERYTHING ELSE
            STA     OP4ADDL,IY
            DEY
            BPL     ERROR1
            CLRI
            LDA     25,IM,HD        SET CLOCK FOR 15 SEC
            STA     MINCLOCK,ZP
ERROR2      LDA     2,IM,HD
            STA     DIGSEL,ZP
            LDA     F0,IM,HD
            ORA     ERRORCNT,ZP     SET ERROR FLAG
            STA     ERRORCNT,ZP
ERROR3      LDA     7F,IM,HD
*           ACC. CONTAINS # OF CONV. CYCLES
RUNDISP     STA     DIGCNT,ZP
RUNDISP1    LDA     FLAGCOM,ZP
            BPL     RUNDISP1
            INC     FLAGCOM,ZP
            JSR     DISPLAY
            DEC     DIGCNT,ZP
            BNE     RUNDISP1        CYCLE UNTIL ZERO
            INC     DIGSEL,ZP
            LDA     7,IM,HD
            CMP     DIGSEL,ZP
            BPL     ERROR3          CYLCE THROUGH 7 DIGITS
            BIT     MINCLOCK,ZP     OUT OF TIME?
            BPL     ERROR2
            JMP     STANDBY
*-------------------------------------
* SUBROUTINE DINCMPY
*      DOUBLE INCREMETN Y AND COMPARE WITH PLSADD LSBYTE
*      C=0,PLAADD>Y; C=1,Y>PLSADD
DINCMPY     INY
            INY
            CPY     PLSADD,ZP
            RTS
* SUBROUTINE PKSRCH8               CYCLES STRTPLS ONCE - LEAVES WHEN IT
PKSRCH8     INC     FLAGCOM,ZP     ENABLE INTERRUPTS
            LDA     0,IM,HD
            JSR     WAITDATA        GET SOME NEW DATA
            BIT     STRTPLS,ZP      HAS STRTPLS GONE TO ONE
            BVC     PKSRCH8         TEST BIT 6
PKSRCH9     LDA     0,IM,HD
            JSR     WAITDATA        GET SOME MORE DATA
            BIT     STRTPLS,ZP      HAS STRTPLS FONE TO 0 AGAIN
            BVS     PKSRCH9         TEST BIT 6
            RTS
* SUBROUTINE FINISH1B
FINISH1B    LDY     2,IM,HD
FINISH1A    DEC     PKADD,ZP
            DEC     OP1ADDL,ZP
            DEY
            BPL     FINISH1A
            TSX
            DEC     259,X
            BPL     FINISH1C
            JSR     ERROR
FINISH1C    RTS
```

```
* SUBROUTINE FINTIME                         TIMES 15 SEC AND RUNS DISPLAY
FINTIME   LDA    25,IM,DD
          STA    MINCLOCK,ZP               INITIALIZE MINCLOCK
FINTIME1  LDA    0,IM,HD                   ZERO FINFLAG SO COME BACK HERE
          STA    FINFLAG,ZP                SET RETURN LOC
          BEQ    DECODE                    GO DECODE ANY SWITHCS
FINTIME2  BIT    MINCLOCK,ZP               HAS CLOCK RUN OUT?
          BPL    FINTIME1
          JMP    STANDBY

* RESET ENTERED UPON POWER ON RESET COMMAND
RESET     LDX    FF,IM,HD                  SET FINFLAG RETURN CODE
          STX    FINFLAG,ZP                SET RETURN LOC
          TXS
          STX    PLSFLG,ZP                 ZERO TO PREVENT TIME LAPSE E5
          CLRD
DECODE    LDA    FF,IM,HD                  INITIALIZE PBSTAT
          STA    PBSTAT,ZP                 SET SO MORE BUTONS CAN BE PUSHED
          STA    PBSTAT+1,ZP
          STA    PBSTAT+2,ZP
          LSR    ,AC                       MAKE ACC=7F
          CLRI
          JSR    WAITDATA                  GO WARM UP A/D
          LDA    1,IM,HD                   SET MASK BIT
          BIT    PBSTAT,ZP                 DATA DISPLAY COMMAND? BIT 0 LOW
          BNEQ   RESET3                    DATA DSIPLAY COMMAND
          JMP    DATADISP
RESET3    BMI    RESET1                    TEMP1?
          JMP    TEMPTUR1                  TEMP1 PUSHED
RESET5    JMP    TEMPTUR2                  GO MEASURE TEMP.  TEMP2
RESET1    BIT    ERRORCNT,ZP               DID WE ERROR OUT LAST TIME?
          BMI    RESET4                    CAN ONLY RESET OR AUTOZERO IF SO
          BIT    PBSTAT+1,ZP               BP DISPLAY COMM.? BIT 0 LOW
          BNEQ   RESET2
          JMP    FINISH4                   LONG JUMP
RESET2    BIT    PBSTAT+2,ZP               IS PULSE DISPLAY COMM.? BIT 7 LOW
          BEQ    RESET5                    TEMP2 IS ACTIVE
          BMI    RESET4                    PULSE
          JMP    FINISH7                   LONG JUMP

*         ACC =1 FROM BEFORE BRANCHES
RESET4    STA    CUFPLS,ZP                 LOOK AT CUFF PRESSURE
          STA    DIGSEL,ZP                 LOOK AT DIGIT #1
          BIT    PBSTAT+1,ZP               RESET?
          BVS    RESET6
          JMP    OUTCODE                   GO OUTSIDE PROM ON D2,PB4
RESET6    BPL    CUFINF
          BIT    FINFLAG,ZP                RETURN TO FINTIME?
          BPL    FINTIME2                  (POW ON).(NO FINFLAG).(NO RES) GO AU
AUTOZERO  LDX    FF,IM,HD
          STX    FCFLAG,ZP                 TELL DATACQ WE'RE TAKING OFFSET DATA
          LDA    7F,IM,HD
          JSR    WAITDATA                  GET CUFF DATA AFTER 80 CYCLES
          SED
          CLRC
          LDA    NEWDATA+1,ZP
          ADC    2,IM,HD
          STA    OFFSET+1,ZP               OFFSET CUFF P. BY 3
          LDA    NEWDATA,ZP
          ADC    0,IM,HD
          STA    OFFSET,ZP                 DEC. ADD & MOVE TO OFFSET
          CLRD
          SEC
          LDA    OFFSET+1,ZP               IS OFFSET =0?
          SBC    2,IM,HD                   SUBTRACT OFF 2
          ORA    OFFSET,ZP                 GET MSD
          BNEQ   CUFINF                    GO TO CUFINF IF NONZERO
          JSR    LOWBATT2                  GO DISPLAY 0

* MAIN PROGRAM - CUFF INFLATION PHASE
*-------------------------------      INITIALALIZATION SECTION
CUFINF    LDX    F7,IM,HD
          LDA    0,IM,HD
ZERODATA  DEX
          STA    CUFDATA,ZPX
          STA    PLSDATA,X
          BNEQ   ZERODATA                  LOOP UNTIL MOST OF PAGE ONE AND ZERO

*-------------------------------
          LDA    NEWDATA,IM,SAL            INTERRUPT IS ENABLED NOW
          STA    OP5ADDL,ZP                MOVE OLDDATA ADD. FO UPPRE DISPLAY
          LDA    OP3ADDL,IM,SAL            POINT UPPER SIPLAY AT OP3ADDL
          STA    OP4ADDL,ZP                MOVE OP3ADDL ADDRESS
          LDA    DIASTRAT,IM,SAH           POINT UP2ADDL AT PAGE
          STA    OP2ADDL+1,ZP              CONTAINING RATIOS
          LDA    00,IM,HD                  CLEAR (BLANK) UPPER DISPLAY
          STA    OP3ADDL,ZP
          STA    OP3ADDL+1,ZP
          STA    PSTOP,ZP                  SET BUBBLE STOPPER
          INC    PLSADL+1,ZP
          LDA    80,IM,HD                  SET TWMPT FLAG TO NO DECIMAL
          STA    TEMPT,ZP
```

```
*                    LDA      100,IM,UD              INPUT AND GET ADULT/CHILD STATUS
                     STA      MINCLOCK,ZP
CUFINF1              LDA      7F,IM,HD               TEST DATA EVERY 128 MS
                     JSR      WAITDATA               GET SOME DATA
                     BIT      MINCLOCK,ZP            TEST IF 1 MIN HAS ELAPSED SINCE ON
                     BPL      CUFINF4
                     JMP      STANDBY                TURNED IT ON AND DIDN'T USE IT
CUFINF4              LDX      0,IM,HD
                     BIT      ADCHILD,ZP             ADULT/CHILD SW BIT 6
                     BVS      CUFINF2
                     LDX      2,IM,HD
CUFINF2              LDA      THRESHLD,X             X=0 ADULT, =2 CHILD
                     STA      OLDDATA,ZP
                     LDA      THRESHLD+1,X           MOVE THRESHOLD TO COMPARE
                     STA      OLDDATA+1,ZP
                     TXA
                     CLRC
                     ADC      DA,IM,HD               ADD ON PROPER A/C DISPLAY
                     STA      DP3ADDL+1,ZP
                     JSR      BCDCOMP
                     BCC      CUFINF1
*------------------------------------               TELL THEM TO STOP PUMPING
                     LDA      5D,IM,HD
                     STA      DP3ADDL+1,ZP            SET UP STOP SIGNAL IN DISPLAY
                     LDA      STRTIM,AB              INITIALIZE CLOCK TO 4 SEC.
                     STA      MINCLOCK,ZP
CUFINF3              LDA      0,IM,HD
                     JSR      WAITDATA               GO GET SOME DATA AND DISPLAY
                     LDA      MINCLOCK,ZP            TEST FOR ZERO IN MINCLOCK
                     BPL      CUFINF3                LOOP UNTIL CLOCK RUNS OUT
CUFINF30             JSR      PKSRCH8                GO FOR FIRST THREE CYCLES OF STRTPLS
*          ALLOW 1.8 SECS BETWEEN PULSES -----------------
                     LDA      3,IM,HD                INITIALIZE PLSWAIT COUNTER
                     STA      PLSWAIT,ZP             ALLW 6 SECONDS
*------------------------------------               REINITIALIZATION SECTION
PKSRCH10             LDA      0,IM,HD
                     STA      PLSFLG,ZP              START TIMING PULSE ARRIVALS
                     STA      OLDDATA,ZP
                     STA      OLDDATA+1,ZP           ZERO OUT OLD DATA FIELD
                     STA      CUFPLS,ZP              SELECT PULSE
                     LDA      2,IM,HD
                     JSR      WAITDATA               WAIT 2 INT. CYCLES FOR DATA AND
*                                                    RUN DISPLAY
*------------------------------------               SEARCH FOR PEAK
*------------------------------------               SEARCH SECTION
PKSRCH1              JSR      BCDCOMP                IS NEWDATA<OLDDATA;C=0?
                     BCC      PKSRCH2                CHECK DATA JUST ACQUIRED
                     LDA      NEWDATA,ZP             NO
                     STA      OLDDATA,ZP
                     LDA      NEWDATA+1,ZP
                     STA      OLDDATA+1,ZP
                     LDA      0,IM,HD
                     JSR      WAITDATA               WAIT FOR NEW DATA AND RUN DISPLAY
                     BMI      PKSRCH1
*------------------------------------               HAVE FOUND PEAK
PKSRCH2              INC      FLAGCOM,ZP             ZERO FLAGCOM
                     INC      CUFPLS,ZP              SELECT CUFF PRESSURE
*          MOVE PULSE PEAK
                     LDY      1,IM,HD
PKSRCH3              LDA      OLDDATA,Y              ACTUAL PEAK IS HERE
                     STA      PLSADD,1Y              MOVE PULSE PEAK
                     DEY
                     BPL      PKSRCH3                GET OTHER BYTE
                     LDA      PLOW+2,ZP
                     JSR      ADDCHK
                     BCS      CYCGO
                     JSR      CLKFLG1
                     BEQ      PKSRCH31
CYCGO                LDA      MINFLG1,ZP
                     BPL      CYCGO2
                     DEC      CYMEM,ZP
                     DEC      CYMEM,ZP
                     BPL      CYCGO1
                     LDA      A,IM,HD                12 BYTE TABLE (6 MEMBERS)
                     STA      CYMEM,ZP               REINITIALIZE CLKMEM POINTER
CYCGO1               LDY      CYMEM,ZP
                     LDA      MINCLK1+1,ZP
                     STA      CLKMEM+1,Y
                     LDA      MINCLK1,ZP
                     STA      CLKMEM,Y
                     JSR      CLKFLG1
                     BEQ      PKSRCH31
CYCGO2               LDA      FF,IM,HD
                     STA      MINFLG1,ZP
PKSRCH31             LDA      3,IM,HD                INITIALIZE PLSWAIT COUNTER
                     STA      PLSWAIT,ZP
*----------                                          PEAK
                     LDA      PLSADD,ZP
                     STA      OLDDATA+2,ZP           POINT ADD. OF OLDDATA AT CURRENT
                     LDX      OLDDATA,IM,SAL         POINT X AT OLDDATA
                     LDY      PLOW,IM,SAL            POINT Y AT PLOW TO START
*------------------------------------                BUBBLE SORT
PKSRCH35             JSR      BCDCOMP1               COMPARE ADJACENT DATA FIELDS
                     BCS      PKSRCH36               QUIT IF NEXT FIELD IS LARGER
```

```
*         X HAS ZP ADD. OF HIGHEST TABLE MEMBER TO SWAP DOWN
SWAP      TYA
          PHA
          LDY       2,IM,HD
SWAP1     LDA       0,ZPX              GET LOW BYTE
          PHA
          LDA       3,ZPX              GET HIGH BYTE
          STA       0,ZPX              PUT IN LOW BYTE
          PLA
          STA       3,ZPX              PUT LOW BYTE IN HIGH BYTE
          INX
          DEY
          BPL       SWAP1              GET REST OF BYTES
          PLA
          CLRC
          ADC       3,IM,HD            POINT OLD Y AT NEXT FIELD
          TAY
          BNEG      PKSRCH35           GO BACK AND BUBBLE SOME MORE
PKSRCH36  INC       PLSADD,ZP
          INC       PLSADD,ZP
* ----------- IS CUFF PRESSURE BELOW 220 MM -------
          JMP       CODEBRK
          DC        X'FF'
DECKEND   BRK
          ORG       BEGIN+3584
CODEBRK   LDX       UPSADDL,ZP
          SEC
          SED
          LDA       CUFDATA+1,ZPX
          SBC       20,IM,HD
          LDA       CUFDATA,ZPX
          SBC       2,IM,HD
          CLRD
          BCC       PKSRCH42
          LDA       0,IM,HD
          LDX       0F,IM,HD
*----------- ZERO OUT MSD OF PEAK TABLE -----------
PKSRCH41  STA       PLOW,ZPX
          DEX
          DEX
          DEX
          BPL       PKSRCH41
PKSRCH42  LDA       PMID2+2,ZP
          JSR       ADDCHK             10 PULSES AFTER PMID2 PULSE?
          BCS       PKSRCH7            GET MORE DATA IF NO
          LDA       PLOW,ZP
          CMP       4,IM,HD
          BCC       PKSRCH37
          CMP       6,IM,HD
          BCC       PKSRCH38
          LDA       1,IM,HD
          STA       OLDDATA,ZP
          LDA       20,IM,HD
          STA       OLDDATA+1,ZP
          BNEG      PKSRCH39
PKSRCH38  LDA       85,IM,HD
          STA       OLDDATA+1,ZP
          BNEG      PKSRCH40
PKSRCH37  LDA       70,IM,HD
          STA       OLDDATA+1,ZP
PKSRCH40  LDA       0,IM,HD
          STA       OLDDATA,ZP
PKSRCH39  LDY       CUFADD,ZP
          DEY
          DEY
          LDX       OLDDATA,IM,SAL
          JSR       BCDCOMPT
          BCS       PKSRCH7
          LDX       PMID2,IM,SAL
          STX       PKADD,ZP
          LDY       2,IM,HD
*         ------------------ CALCULATE TEST DIASTOLIC THRES
          LDA       DIASTRA1,IM,SAL
          STA       UP2ADDL,ZP         PREPARE FOR MULTIPLY
          JSR       PROCESS1           BEGINNING PROCESSING
PROCESS5  JSR       DINCMPY
          BCS       PKSRCH7
          JSR       BCDCOMP1
          BCS       PROCESS5           GO SEARCH FOR FIRST PEAK BELOW
          JSR       DINCMPY            DIASTOLIC THRESHOLD
          BCS       PKSRCH7            HAVE ENOUGH DATA?
          JSR       BCDCOMP1           FIND SECOND PEAK BELOW DIASTOLIC
          BCC       FINISH             THRESHOLD
          BCS       PROCESS5
PKSRCH7   JSR       PKSRCH8            WAIT UNTIL BEGINNING OF NEXT PULSE
          LDY       1,IM,HD
PKSRCH4   LDA       NEWDATA,Y
          STA       CUFADD,1Y          MOVE CUFF PRESSURE INTO PLACE
          DEY
          BPL       PKSRCH4
```

```
                LDA     CUFADD,ZP         POINT LOWER DISPLAY AT CURRENT
                STA     UP5ADDL,ZP         VALUE OF CUFF PRESSURE
                LDA     PLSADD,ZP         CHECK NO. IN BUFFER
                STA     CUFADD,ZP         POINT AT NEXT CUFF CELL
                CMP     AA,IM,HD
                BCS     FINISH
PKSRCH11        JMP     PKSRCH10          MAKE LONG JUMP
FINISH          LDA     PMID3,IM,SAL      POINT MULTIPLICAN AT
                STA     UP1ADDL,ZP          AT PMID3 TO START
                LDA     PMAX,IM,SAL       SAVE PMAX LOCATION TEMPORARILY
                STA     PKADD,ZP
                LDA     3,IM,HD
                STA     PLSFLG,ZP
                PHA
FINISH1         LDA     PEAKSCLH,IM,SAL
                STA     OP2ADDL,ZP
                JSR     BCDMULT           MULTIPLY LOWER PEAK BY RATIO
                LDX     PKADD,ZP          POINT X AT PM AX TO BEGIN
                LDY     PRODUCT+1,IM,SAL
                JSR     BCDCOMPT          COMPARE THRM
                BCS     FINISH2           ARE THEY LESS THAT ALLOWED
                JSR     FINISH1B
                BPL     FINISH1           GO AROUND UNTIL A PAIR SATISFIES TIS
FINISH2         LDA     PKSCLL,IM,SAL
                STA     OP2ADDL,ZP        POINT AT PEAK RATIO
                LDA     PKADD,ZP
                STA     OP1ADDL,ZP        POINT AT PEAKIN PAGE ONE
                JSR     BCDMULT           MULTIPLY
*               SCALED PEAK (PKADD POINTER) IS IN PRODUCT+1,2
                LDX     PKADD,ZP
                LDY     2,ZPX             GET ADD. OF PEAK ((PKADD)+2)
                DEY
                DEY
                DEY
                DEY
                LDX     PRODUCT+1,IM,SAL  POINT AT SCALED PEAK
                JSR     BCDCOMP1          COMPARE 2 NEIGHBORS AHEAD
*               PULSE 2 AHEAD OF PEAK IS POINTED AT BY Y
*               IS THIS PULSE > 0.66 OF PEAK PULSE
                BCC     FINISH2A
                TYA
                ADC     7,IM,HD           POINT Y AT 2 PULSES BEHIND PEAK, C=1
                TAY
                JSR     BCDCOMP1          COMPARE TO SCALED PEAK
                BCS     FINISH2B
FINISH2A        JSR     FINISH1B
                BPL     FINISH1
FINISH2B        LDX     PKADD,ZP
                LDY     2,IM,HD
                LDA     DIASTRAT,IM,SAL   POINT OP2ADDL AT DIASTOLIC RATIO
                STA     OP2ADDL,ZP
                JSR     PROCESS1
*               ---------- DIASTOLIC LOOP
FINISH3         JSR     DINCMPY
                BCS     FINISH3A
                JSR     BCDCOMP1          X HAS PULSE ADD.
                BCS     FINISH3
                JSR     DINCMPY
                JSR     BCDCOMP1
                BCC     FINISH3B
                CPY     PLSADD,ZP         SEE IF WE'RE OUT OF DATA
                BCC     FINISH3
*               ----------
FINISH3A        JSR     ERROR             GO ERROR OUT
FINISH3B        TYA
                SBC     3,IM,HD           DEC. Y 4 TIMES
                STA     DICUFADD,ZP
* ------------------------------ FIND SYSTOLIC PRESSURE
FINISH9         LDA     SYSTRAT,IM,SAL
                STA     OP2ADDL,ZP
                LDX     PKADD,ZP
                LDY     2,IM,HD
                JSR     PROCESS1
* ---------- NEW SYSTOLIC LOOP -------- SEARCH FROM MIDDLE FORWARD
FINISH3C        DEY
                DEY
                BMI     FINISH3A          HAVE RUN OUT OF DATA
                JSR     BCDCOMP1          COMPARE
                BCS     FINISH3C
                DEY
                DEY
                BMI     FINISH3A          HAVE RUN OUT OF DATA
                JSR     BCDCOMP1
                BCS     FINISH3C
                TYA
                ADC     4,IM,HD           BACK UP Y 2 PULSES
                STA     SYCUFADD,ZP
* ---------- END OF SYSTOLIC LOOP --------------
                LDX     7,IM,HD           ZERO OUT
                LDA     0,IM,HD
```

```
T61     STA     PRODUCT,ZPX     PRODUCT AND MCANDTMMP
        DEX
        BPL     T61
        LDY     8,IM,HD
T11     CLRC
        LDX     1,IM,HD
T16     LDA     PRODUCT,ZPX
        ADC     CLKMEM,Y
        STA     PRODUCT,ZPX
        DEY
        DEX
        BPL     T16
        TYA
        BPL     T11
T15     CLRC
        LDX     1,IM,HD
T17     LDA     PLSCNT1,ZPX     BINARY ADD TWO BYTE TIME INTERVALS
        ADC     PRODUCT,ZPX
        STA     PLSCNT1,ZPX
        DEX
        BPL     T17
        SED
        SEC
        LDX     1,IM,HD
T12     LDA     PULSECNT,ZPX    DECIMAL ADD PULSE COUNT
        ADC     0,IM,HD
        STA     PULSECNT,ZPX
        DEX
        BPL     T12
        CLRD
        SEC
        LDA     PLSCNT1+1,ZP
        SBC     TEST+1,AB       FIND WHEN TO STOP
        LDA     PLSCNT1,ZP
        SBC     TEST,AB
        BCC     T15
* --------- HAVE WE GOTTEN 16
        LDA     PLSADD,ZP
        CMP     32,IM,DD        DO WE HAVE 16 PULSES
        BCC     T21
*        FIND PULSE PRESSURE ----- MUST BE GREATER THAN 10 MM
        LDY     1,IM,HD
        SEC
        SED
        LDA     SYCUFADD,IY
        SBC     10,IM,DD
        SBC     DICUFADD,IY
        DEY
        LDA     SYCUFADD,IY
        SBC     DICUFADD,IY
        BCS     FINISH4
T21     JSR     ERROR           GO TO ERROR
*-------------------------------  DISPLAY BLOOD PRESSURE FOR 15 SEC
* ----- PB7.D2 ---------
FINISH4 LDA     SYCUFADD,ZP     POINT UPPER DISPLAY AT
        STA     OP4ADDL,ZP        SYSTOLIC PRESSURE
        LDA     DICUFADD,ZP     POINT LOWER DISPLYA AT
        STA     OP5ADDL,ZP        DIASTOLIC PRESSURE
        JMP     FINTIME         RUN 15 SEC
* ----------- PB5.D1 -----------
*------------------------------  DISPLAY PULSE RATE
FINISH7 LDA     00,IM,HD        BLANK OP3ADDL
        STA     OP3ADDL,ZP
        STA     OP3ADDL+1,ZP
        LDA     OP3ADDL,IM,SAL
        STA     OP4ADDL,ZP      POINT UPPER DISPLAY AT BLANKS
        LDA     PULSECNT,IM,SAL
        STA     OP5ADDL,ZP      POINT AT PULSE RATE
        JMP     FINTIME         RUN 15 SEC
* SUBROUTINE ADDCHK             CHECK ADD. WITH END OF DATA FIELD
ADDCHK   CLRC
         ADC    20,IM,DD
         CMP    PLSADD,ZP
         RTS
* SUBROUTINE STANDBY - NO EXIT - TURNS POWER OFF
STANDBY LDA     FF,IM,HD
        STA     DATAPBR,AB      SET PB3=1
        STA     DATAPBDR,AB     MAKE PB OUTPUT
        INC     DATAPBR,AB      MAKE PB3=0
        DEC     DATAPBR,AB      MAKE PB3=1 AGAIN
STANDBY1 JMP    STANDBY1        AN INFINITE LOOP
*              ----- PWER IS NOW OFF ----------
```

TABLE I A

| Address (Bytes) | Mnemonic | Description |
|---|---|---|
| 000 ↓ 0A9 | CUFDATA | Stored Cuff Pressure data (2 bytes each) |
| 0AA(2) | PLSADD | Address of Pulse |

TABLE I A-continued

| Address (Bytes) | Mnemonic | Description |
|---|---|---|
| OAC(2) | CUFADD | Address of Cuff Pressure |
| OAE(2) | OP1ADDL | OP1 address low - used to point at the multiplic and for BCDMULT (BINMULT) |
| OB0(2) | OP2ADDL | Used to indicate the multiplier |
| OB2(2) | OP3ADDL | Symbol storage for upper display |
| OB4(2) | OP4ADDL | Address of word to be displayed in the upper display. |
| OB6(2) | OP5ADDL | Address of the word to be displayed in the lower display. |
| OB8(1) | DISPWORK | Used by the DISPLAY subroutine to assemble output code to PA register. |
| OB9(1) | TEMPT | Temperature flag, 0 = Temp, 80 = other This flag is used for the decimal point during full strobed display. |
| OBA(2) | TIMINTCY | Timer interrupt cycle counter. TIMINTCY + 1 stores value of 64 $\mu$sec timer and counts upward while TIMINTCY is decremented from $36_D$ for 16.4 msec/unit. $36_D$ therefore is 0.59 sec. MINCLOCK is decremented each 0.59 sec (as is PLSWAIT if PLSFLAG = 0). |
| OBC(1) | MINCLOCK | Hundredths of a minute binary counter - used for counting 15 seconds and 1 minute. Run by TIMINTCY (Internal Timer) |
| OBD(1) | MINFLG1 | Alternate timer flag. FF indicates this pulse time will be read, 00 indicates skip pulse time on this pass. |

TABLE I B

| Address (Bytes) | Mnemonic | Description |
|---|---|---|
| OBE(2) | MINCLK1 | Main pulse rate timer. This clock is incremented every 16.4 msec just after TIMINTCY is decremented. |
| OC0(1) | PLSFLG | PLSWAIT disable flag (disable $\neq$ 0). |
| OC1(1) | PLSWAIT | Maximum allowed delay between pulses (3 = 1.8 seconds). Only decremented from 3 if PLSFLG = 0. |
| OC2(4) | DATAINTMP | Input working storage (See DATACQ) |
| OC6(1) | DATAREG | PA register save area during the read cycle time. |
| OC7(1) | FLAGCOM | Flag register - FF (LOAD) indicates that a pass through IRQ - DATACQ has been completed. Used in WAITDATA and RUNDISP to establish a "wait until interrupt" loop. |
| OC8(2) | NEWDATA | Packed BCD working storage. Contains the displayed cuff pressure whenever the lower display continuous displays the cuff pressure without pulse or calculation locking. |
| OCA(3) | OLDDATA | Contains the packed BCD prior leading edge pulse height data for comparison to find the maximum height of a single pulse. Also contains address of OLDDATA in Pulse table. |
| OCD(3) | PLOW | Lowest peak in the peak table with 8 bit address included in PLOW + 2. CLKMEM storage starts 11 pulses after (PLOW + 2). PLOW is also used as a test for the record pulse height. For PLOW in the range (1) <400, (2) <PLOW <600, or (3) PLOW >600, the maximum final stop pressure for the measurement is (1) 75, (2) 85, or (3) 120 mm HG. |
| OD0(3) | PMID1 | Next highest peak in the peak table with its corresponding address in PMID1 + 2. |

TABLE I C

| Address (Bytes) | Mnemonic | Description |
|---|---|---|
| OD3(3) | PMID2 | Next highest peak in the peak table with 8 bit address. This address is also used to eliminate auscultatory gaps by requiring DATACQ to continue until 10 pulses beyond |

TABLE I C-continued

| Address (Bytes) | Mnemonic | Description |
|---|---|---|
| | | (PMID2 + 2). The PLOW - PMID2 peak set is used for worst case determination of the diastolic pressure with (PMID2 + 2) used as the address to start diastolic and systolic search. Data acquisition will continue until the program can find a valid diastolic pressure for this peak set. |
| OD6(3) | PMID3 | Next highest peak in the peak table with its corresponding address. |
| OD9(3) | PMID4 | Next highest peak in the peak table with its corresponding address. |
| ODC(3) | PMAX | Highest peak in the peak table. |
| ODF(2) | PSTOP | Contains 9900 as the stop for the bubble sort during the bubble sort period. ERRORCNT is equated with the least significant digits in program assembly = PSTOP + 1. |
| OE1(1) | PKADD | Address of the highest peak table set kept as valid after artifact rejection. The sequence is:<br>DC = No artifacts<br>D9 = One artifact<br>D6 = Two artifacts<br>D3 = Three artifacts<br>More than three artifacts causes error (E3) |
| OE2(2) | PEAKAV | Sum of the three highest peaks (after artifact elimination at the end during display) |
| OE4(2) | SYCUFADD | Systolic cuff pressure address |
| OE6(2) | DICUFADD | Diastolic cuff pressure address |
| OE8(1) | MULTIDIG | Isolated multiplier digit |

TABLE I D

| Address (Bytes) | Mnemonic | Description |
|---|---|---|
| OE9(1) | DIGCNT | Number of multiplier digits less one. Also number of waitdata internal loops (must be <7F) |
| OEA(4) | PRODUCT | Product field (8 digits long) |
| OEE(4) | MCANDTMP | Multiplicand right justified here - (Equate statements in assembly overlap this storage with PLSCNT1 = MCANDTMP and PULSECNT = MCANDTMP + 2) |
| OF2(1) | CYMEM | Cyclic memory offset for time between two pulses. This causes the next time acquired to be stored in the next memory cell. |
| OF3(1) | CUFPTR | Cuff pointer - "Cuff Table" address pointer. |
| OF4(1) | PKPTR | Peak pointer - "Peak Table" address pointer. |
| OF5(1) | FINFLAG | Fintime return flat = 0 |
| OF6(1) | FCFLAG | Indicates to DATACQ when the program is taking offset (antozero data). |
| OF7(1) | Not Used | Blank area. Addresses above this in page zero are not reintialized. |
| OF8(1) | CUFPLS | Communicates with DATACQ as to whether the cuff pressure or pulse height will be read from the A-D. Cuff pressure = 1, Pulse = 0. |
| OF9(1) | DIGSEL | Indicates which digit will be displayed in the multiplexed digit display. |
| OFA(3) | PBSTAT STRTPLS BPPULSE ADCHILD | See Table 2.5, Chapter II, page 43. |
| OFD(2) | OFFSET | Cuff Pressure plus 2 mm Hg acquired on autozero which is subtracted from each cuff pressure read thereafter. |
| 100 ↓ 1A9 | PLSDATA | Page one pulse height data storage |

TABLE I E

| Address (Bytes) | Mnemonic | Description |
|---|---|---|
| 1AA ↓ | CLKMEM | Clock memory for pulse rate stored 2 bytes each, six words long. |

TABLE I E-continued

| Address (Bytes) | Mnemonic | Description |
|---|---|---|
| 1B5 | | |
| Upper Address Variables | | |
| FEB(2)$_D$ | ADTHRESH | Adult threshold = 0285. |
| FED(2)$_D$ | CHTHRESH | Child threshold = 0160. |
| FEF(2)$_D$ | DIASTRAT | Diastolic ratio times one-third = 0025. |
| FF1(2)$_D$ | SYSTRAT | Systolic ratio times one-third = 0015. |
| FF3(2)$_D$ | PKSCLL | Minimum Height percentage for a pulse two away from the peak = 0066. |
| FF5(2)$_D$ | PEAKSCLH | Maximum percent in height from the low to the high peak of three in the peak table = 0125. |
| FF7(2)$_X$ | TEST | Binary value at which pulse iteration ceases when calculating the pulse rate. |
| FF9(1)$_X$ | STRTIM | Number of 0.8 second delays after "start" before pulse acquisition begins = 05. |
| FFA(2) | NMI | Vector address for NMI = Address OA9B. |
| FFC(2) | RES | Vector address for processor reset = Address OA9B. |
| FFE(2) | IRQ | Vector address for IRQ = Address 08AO. |
| Mnemonics equated in page zero to save storage | | |
| OEO(1) | ERRORCNT = PSTOP + 1 | Error counter for pulse wait clock. |
| OEE(2) | PLSCNT1 = MCANDTMP | Pulse rate counter. |
| OFO(2) | PULSECNT = MCANDTMP + 2 | Other pulse rate counter. |

Referring to FIG. 9, there is shown an analog system which may be used for the measurement of blood pressure in accordance with the invention. This analog system is operative to compute the diastolic and systolic pressures on the basis of the percent of peak of a peak reference value as was explained above in connection with FIG. 8. The system utilizes a cuff 12 which is located on an arm 10 or other extremity. The cuff is inflated by way of a pump 14 and deflated through an air bleed valve 16 as was explained in connection with FIG. 1. A transducer 18 provides an electrical signal corresponding to the cuff pressure upon which the pulsatile signals due to the pumping action of the heart are superimposed. This electrical signal is amplified in an amplifier 110. The output of the amplifier is the cuff pressure signal. The pulsatile signal is obtained by filtering the cuff pressure signal in a bandpass filter 112. A direct current (DC) blocking and clamp circuit 114 is used to establish a level of this pulsatile signal such that the pulses in the train will all be above zero amplitude at which the train is clamped.

The pulse train is applied to an envelope detector 116 which provides an output signal which follows the peaks of the pulses in the train. A peak detector and hold circuit 118, as may be implemented by a resistance capacitance circuit having rapid charge and slow discharge characteristics, provides an output voltage equal to the peak amplitude of the envelope. This output voltage as well as the signal from the envelope detector is produced during the deflation or bleed cycle of the cuff, i.e., after the cuff has been inflated to occlude the artery in the arm and then allowed to deflate at a controlled rate by opening the valve 16.

The output voltage from the peak detector is utilized as the peak reference level. A multiplier 120 provides the systolic reference by multiplying the peak reference voltage from the peak detector 118 by 0.45. Another multiplier 122 outputs the diastolic reference by multiplying the peak reference from the peak detector 118 by 0.75.

The systolic event is located by a comparator 124. The diastolic event is located by another comparator 126. The output signal from the envelope detector is delayed in a delay circuit 128, such for example as a so-called bucket brigade delay line. The delay interposed is sufficient to compensate for the propagation of the envelope detector output signal to the peak detector 118 and multiplier circuits 120 and 122. The output of the comparator is a voltage which drops from high to low potential when the envelope detector output signal is of an amplitude equal to the predetermined percentage of the peak reference level (viz, equal to the systolic threshold level as provided by the output of the multiplier 120). Similarly the output of the comparator 126 switches from high to low level when the envelope reaches the diastolic threshold. The output of the comparator 126 is inverted in an inverter amplifier circuit 130 so as to operate a latch 132.

The latch 132 is set so as to provide a high output (level "1" shown at the output at the latch) on a negative-going transition, and a low output (level "2") on a positive-going transistion. A positive-going transition occurs when the output of the comparator 126 goes low which occurs when the delayed envelope detector output signal reaches the diastolic threshold level. Until the diastolic threshold level is reached, the high level latch output controls an analog gate circuit 134 which switches the cuff pressure signal from the transducer amplifier 110 to a hold circuit 136. The output of the hold circuit is applied to a display 138. This display 138 may be a digital display such as includes LEDs which is driven by an analog to digital converter to which the output of the hold circuit is applied. Alternatively, the display 138 may be a meter calibrated in terms of blood pressure. The hold circuit 136 is not actuated, as by switching in a holding capacitor through a gating diode which is biased by the output voltage from the latch 132. So long as the hold circuit 136 is not actuated, the display 138 shows the cuff pressure. The operator may observe the display 138 while inflating the cuff 12 and the display 138 will indicate when the cuff is inflated to the desired maximum pressure (suitably 285 mm Hg for adult blood pressure measurements, and 160 mm Hg for the blood pressure measurements on children). When the bleed valve 16 is open, the bleed rate can be checked by watching the display 138.

The cuff pressure signal is delayed in a delay circuit 140 which compensates for propagation delay in the rest of the system. The delayed blood pressure signal is applied to a sample and hold circuit 142. When the systolic comparator 124 provides a negative-going transition, as will be the case on the detection of the systolic event, a Schmidt trigger circuit 144 or other suitable one-shot multivibrator, is triggered to produce a sampling pulse. During the time of this pulse the sample and hold circuit 142 acquires the cuff pressure signal which was produced at the time of the systolic event. This cuff pressure signal is applied to a systolic display 146 which may be a digital display or a meter as described in connection with the diastolic display 138.

When the output of the latch 132 goes low, the analog gate is switched to apply the delayed cuff pressure signal to the hold circuit 136 which is simultaneously actuated to hold the voltage. The held voltage is then applied to the diastolic display 138. Accordingly, both the systolic and diastolic pressures will be indicated.

From the foregoing description it will be apparent that there has been provided an improved method for blood pressure measurement which can also be used to measure pulse rate. Apparatus for carrying out the method is also described. It is believed that the system described in connection with FIGS. 1 through 6 will provide more accurate blood pressure measurement, although the analog system, as described in connection with FIG. 9, has advantages of savings in cost. Variations and modifications in the herein described method and apparatus, will undoubtedly suggest themselves to those skilled in the art. Accordingly, the foregoing description should be taken merely as illustrative and not in any limiting sense.

What is claimed is:

1. The method of measuring blood pressure by the use of the arterial pressure pulses which accompany the temporary constriction of an artery by means of a compression cuff or the like, said method comprising the steps of selecting, and storing signals corresponding to, a plurality of pulses which consist of the highest pulses in a group of said pressure pulses regardless of the order of their occurrence during said temporary constriction, detecting from said highest pulses a reference level, and then providing outputs corresponding to the pressure exerted by the blood in said artery upon occurrence of first and second pulses in said group, respectively preceding and following at least one of said highest pulses, which first and second pulses bear certain amplitude relationships to first and second levels which are in predetermined proportional relationship with said reference level, the one of said outputs provided upon occurrence of said first pulse corresponding to the systolic blood pressure and the other of said outputs provided upon occurrence of said second pulse corresponding to the diastolic blood pressure.

2. The invention as set forth in claim 1 further comprising the steps of timing the occurrence of a number of said pressure pulses, said number being more than two, and providing an output pulse rate corresponding to the time interval during which said number of said pulses occur.

3. The invention as set forth in claim 2 including the step of selecting said number of pulses for timing from those of said pressure pulses which occur approximately when one of said first and second pulses occurs.

4. The invention as set forth in claim 1 wherein said detecting step is carried out while said artery is being constricted.

5. The invention as set forth in claim 1 wherein said detecting step is carried out while the constriction of said artery is being released.

6. The invention as set forth in claim 1 wherein said method further comprises the step of detecting the static pressure applied by said cuff and providing said outputs from the detected static pressures which are concurrent with said first and second pulses.

7. The invention as set forth in claim 1 wherein said predetermined proportional relationship which said first level bears to said reference level is approximately forty-five percent, and said proportional relationship which said second level bears to said reference level is seventy-five percent.

8. The invention as set forth in claim 7 wherein said amplitude relationships of said first pulse to said first level and said second pulse to said second level are:

that said first pulse is a member of a first set of three pulses, two of which are adjacent and have amplitudes lower than said first level and the other of which has an amplitude at east equal to said first level and is the closest of said pulses in said first set to said one highest amplitude pulse, said other pulse of said first set being said first pulse; and that said second pulse is a member of a second set of three pulses, two of which are adjacent and have amplitudes lower then said second level and the other of which has an amplitude at least equal to said second level and is the closest of said pulses in said second set to said one highest amplitude pulse.

9. The method of obtaining information as to the vascular condition of a body comprising the steps of producing a change in circulation through a blood vessel and generating electrical signals corresponding thereto, translating said signals into a train of pulses which correspond to the pressure pulsations in said blood vessel as said circulation changes, deriving from a plurality of pulses in said train which are of the highest amplitude pulses in said train and certain of which have predetermined amplitude relationship with respect to the pulse of highest amplitude in said plurality of pulses, a reference level corresponding to the average peak level thereof, detecting those of said pulses in said train having amplitudes which are approximately of amplitudes which are certain percentages of said reference level, and providing outputs representing said information from those of said electrical signals which are substantially coincidental with said pulses.

10. The invention as set forth in claim 9 wherein said detecting step is carried out by detecting first and second pulses which respectively precede and succeed at least one of said plurality of pulses of highest amplitude.

11. The invention as set forth in claim 10 wherein said detecting step is carried out by detecting, as said first pulse and second pulse, pulses having amplitudes which are different percentages of said reference level.

12. The invention as set forth in claim 11 wherein said first pulse is a member of a first set of at least three adjacent pulses in said train one of which is of amplitude equal to or greater than a first of said different percentages of said reference level and the others of which are of amplitudes less than said first percentage of said reference level, said first pulse being the one of said pulses in said pair of amplitude equal to or greater than said first percentage of said reference level and which is closest to said one pulse of highest amplitude, and wherein said second pulse is a member of a second set of at least three adjacent pulses in said train one of which is of amplitude equal to or greater than a second of said different percentages of said reference level and the others of which are of amplitude less than said second percentage of said reference level, said second pulse being the member of said second pair of amplitude equal to or greater than said second percentage of said reference level and which is closest to said one pulse of highest amplitude level.

13. The invention as set forth in claim 12 wherein said information is systolic and diastolic blood pressure and said first percentage is about 45% and said second percentage is about 75%, said output coincident with said first pulse representing said systolic pressure and said output coincident with said second pulse representing said diastolic pressure.

14. The invention as set forth in claim 13 including the steps of timing the duration of the total time between a plurality of pairs of said pulses which occur sequentially in said train, and
deriving another output representing pulse rate from the said duration of said sequentially occurring pulses.

15. The invention as set forth in claim 12 wherein said deriving step is carried out by selecting a set of pulses of highest amplitude, the highest amplitude one of which is at most 25% higher than the amplitude of the lowest pulses in said set and said highest amplitude one of said pulses is no more than 150% of both of a pair of pulses which are consecutive therewith and are next adjacent thereto.

16. The invention as set forth in claim 15 including the step of detecting an error in said information when less than a certain number of pulses occur in said train.

17. The invention as set forth in claim 16 wherein said error detecting step includes detecting an error when said first pulse is the first pulse in said train.

18. The invention as set forth in claim 17 wherein said error detecting step includes detecting an error when less than a certain number of pulses occur in said train after said second pulse.

19. The method of obtaining information as to blood pressure comprising the steps of
providing electrical signals corresponding to the constriction pressure exerted on a blood vessel as the constriction thereof is changed,
translating said electrical signals into a train of successive pulses each corresponding to a successive pulsation of said vessel and having an amplitude which is a function of the pulsatile component of the blood pressure,
translating said electrical signals into first digital signals each corresponding to a different one of said pulses in said train and representing the amplitude of said electrical signals when each of said pulses in said train occur, which first digital signals represent the constriction pressure on said vessel,
storing all said first digital signals,
storing all second digital signals representing the amplitudes of said pulses in said train,
developing from said pulses in said train a reference level corresponding to the average of the amplitudes of a set of those of said pulses in said train which are of highest amplitude level regardless of where they occur in said train,
identifying from said stored second digital signals first and second pulses in said train respectively having amplitudes at least equal to a systolic threshold level and a diastolic threshold level each of which are different percentages of said reference level, and
displaying as systolic blood pressure and as diastolic blood pressure the values of said first digital signals respectively corresponding to said first pulse and to said second pulse.

20. The invention as set forth in claim 19 wherein said developing step includes the steps of storing a peak table of third digital signals which correspond to those pulses in said train which are of highest amplitude, said third digital signals each representing the amplitude of a different one of said highest amplitude pulses,
selecting those of said third digital signals which correspond to three pulses in said train and have amplitudes, the highest of which is at most a first predetermined percentage of the smallest and the highest of which is at most a second predetermined percentage of the amplitudes of each of the pair of pulses next adjacent thereto in said train, said three pulses constituting said set, and
obtaining from said third digital signals corresponding to the pulses in said set, a digital signal representing said reference level.

21. The invention as set forth in claim 20 wherein said identifying step includes the step of selecting said first and second pulses from said stored second digital signals located on opposite sides of the one of said second digital signals which corresponds to one of said highest amplitude pulses, said vessel being in a more constricted condition while the pulses on the one of said opposite sides which includes said first pulse are being produced than while the pulses on the other of said opposite sides which include said second pulse are being produced, and said first and second pulses being members of first and second sets of at least three pulses which correspond to digital signals of values one of which is at least equal to said systolic and diastolic threshold values respectively and the other two of which are both less than said systolic and diastolic threshold values respectively, said one pulse of said set being closest to said highest amplitude pulses and said first and second pulses being said one pulses of their respective sets.

22. The invention as set forth in claim 21 including the step of measuring the intervals of time between the pulses of each pair of pulses in said train and inhibiting the displaying of said pressures if more than a predetermined number of said intervals are greater than a given length.

23. The invention as set forth in claim 22 including the step of inhibiting the displaying of said systolic pressure if said first pulse corresponds to the one of said second digital signals which is located at an end of said table.

24. The invention as set forth in claim 23 including the step of also inhibiting the displaying of said pressures if less than a certain number of second digital signals are stored.

25. The invention as set forth in claim 24 including the step of also inhibiting the displaying of said pressures unless the values of the one of the first digital signals corresponding to said first pulse is at least the sum of the value of said first digital signal corresponding to said second pulse and a value corresponding to a certain pressure which is lower than any normal blood pressure difference between systolic and diastolic pressures.

26. The invention as set forth in claim 20 wherein the constriction of said vessel is changed by applying pressure with the aid of a cuff externally to the body member which carries said blood vessel and releasing said pressure, and said step of providing electrical signals is carried out by transducing said cuff pressure into said electrical signals as said cuff pressure changes in one of two opposite senses, in the first of which said pressure is applied and in the second of which said pressure is released, and wherein said step of storing said second digital signals is carried out to provide a pulse table of said second digital signals representing the heights of said pulses as said cuff pressure changes in said one sense from a first cuff pressure to a second cuff pressure, and said step of storing said first digital signals is carried out to provide a cuff table of said first digital signals representing the static pressure presented by said cuff when each of said pulses occur as said cuff pressure changes from said first cuff pressure to said second cuff pressure, and said steps of storing said first and second digital signals in said pulse table and in said cuff table are carried out until certain digital signals in said tables satisfy predetermined criteria.

27. The invention as set forth in claim 26 wherein said criteria are that
(a) at least a certain number of said second digital signals are stored in said pulse table after the storage of the one of said second digital signals which corresponds to a pulse near the middle of said peak table between approximately like numbers of digital signals corresponding to pulses of higher amplitude and of lower amplitude which are also stored in said peak table,
(b) the one of said first digital signals in said cuff table which represents the last cuff pressure in said cuff table has a value which is predetermined by the value of the third digital signal representing the lowest one of the pulses in said peak table, and
(c) there are at least two consecutive second digital signals stored in said pulse table after the storage of said one of said second digital signals which corresponds to said pulse near the middle of said peak table which represents values below a predetermined threshold value corresponding to a predetermined percentage of the average of the three lowest third digital signals in said peak table.

28. The invention as set forth in claim 27 wherein said first and second digital signals are stored in said pulse table and said cuff table nevertheless until said tables are fully occupied even if any of said criteria remain unsatisfied.

29. The invention as set forth in claim 27 wherein said systolic threshold value is 0.45 times the said average from the amplitudes of said set of three highest third digital signals in said peak table and said diastolic threshold is 0.75 times said last named average.

30. The invention as set forth in claim 27 including the step of obtaining information respecting pulse rate by first measuring the time interval for the occurrence of a group of said pulses the first of which occurs after the occurrence of a plurality of pulses commencing with the pulse following the pulse which corresponds to the digital signal in said peak table having the lowest amplitude, obtaining said pulse rate information in terms of the average rate at which the pulses in said group occurs.

31. The invention as set forth in claim 27
wherein said identifying step includes the steps of
obtaining from said reference level said diastolic threshold level in terms of the product of average level of the pulses in said set and a factor which is about 0.75,
obtaining from said reference level said systolic threshold in terms of the product of said average level of the pulses in said set and a factor which is about 0.45,
selecting a set of said second digital signals in said pulse table from those second digital signals therein which correspond to three consecutive pulses more than two pulses beyond the pulse which is located in the middle of said peak table on the side of said middle pulse in the direction of lower cuff pressures, which said set of second digital signals represent two values below said diastolic threshold level and one value at least equal to said diastolic threshold level, said digital signal having a said one value corresponding to said second pulse, and
selecting another set of second digital signals in said pulse table from those second digital signals which correspond to three consecutive pulses more than two pulses beyond the pulse which is located in the middle of said peak table in the direction of higher cuff pressures, which said another set of second digital signals represent two values below and one value at least equal to said systolic threshold level, said digital signal having said one value corresponding to said first pulse.

32. Apparatus for obtaining physiological information from the pressure exerted by a blood vessel which comprises
(a) means for producing a pair of electrical signals a first of which is a function of the pressure exerted by said blood vessel as a changing constricting pressure is applied thereto and a second of which is a function of the pulsatile component of said pressure and is in the form of a train of pulses each for a successive blood pressure pulse,
(b) means for converting said first and second signals into first and second digital signals,
(c) a programmed data processor responsive to said first and second digital signals having means for
(1) acquiring and storing said first and second digital signals upon occurrence of each of said pulses and a group of said second digital signals of highest amplitudes,
(2) locating one of said second digital signals the value of which has a certain relationship to the average of the peak value of a plurality of the second digital signals in said group, and was acquired after a member of said second digital signals in said group when said constricting pressure changes in a decreasing sense and before said member of second digital signals in said group when said constricting pressure changes in an increasing sense, (3) producing an output corresponding to the value of said first digital signal which is acquired for the same one of said pulses in said train as said one of said second digital signals to represent the diastolic blood pressure.

33. The invention as set forth in claim 32 wherein said programmed data processor further comprises means for (4) locating another of said second digital signals the value of which has another certain amplitude relationship to said average of the peak value of second digital signals in said group, and was acquired before said member of said second digital signals in said group when said constricting pressure changes in a decreasing sense and after said second digital signals in said group when said constricting pressure changes in an increasing sense, and (5) producing another output corresponding to the value of said first digital signal which is acquired for the same one of said pulses as said another of said second digital signals to represent the systolic blood pressure.

34. The invention as set forth in claim 33 wherein said processor further comprises means for (6) eliminating the effect of pulses which are artifacts including means for including in said group only such of said second digital signals which have values which satisfy certain relationships.

35. The invention as set forth in claim 34 wherein said processor further comprises means for (7) computing pulse rate from the time interval for the acquisition of a plurality of said digital signals in another group which are acquired after said first named group.

36. The invention as set forth in claim 35 wherein said programmed data processor is a microcomputer having memories for the storage of the program and for said first and second groups of digital signals.

37. The invention as set forth in claim 36 wherein said apparatus further comprises display means responsive to said outputs from said data processor for indicating the numerical value of said systolic and diastolic pressures and said pulse rate.

38. The invention as set forth in claim 32 wherein said means for producing said electrical signals includes transducer means for providing an analog signal which is proportional to said pressure, said analog signal providing said first signal, and means for filtering said analog signal so as to pass frequencies in said pulsatile component for providing said second signal.

39. The invention as set forth in claim 38 wherein said converting means includes analog to digital converter means, switching circuit means for selectively applying one of said first and second signals to said analog to digital converter means, and means for generating a control signal in response upon occurrence of each pulse of said second signal, said processor also having means responsive to said control signals for operating said switching means to apply said second signal to said analog to digital conversion means whereby to present said first and second digital signals to said processor for acquisition upon occurrence of each of said pulses in said train.

40. Apparatus for obtaining information as to the vascular condition of a body comprising means for producing a change in circulation through a blood vessel and generating electrical signals corresponding thereto, means for translating said signals into a train of pulses which correspond to the pressure pulsations in said blood vessel as said circulation changes, means for deriving from a plurality of pulses in said train which are of the highest amplitude and certain of which have predetermined amplitude relationships with the pulse of highest amplitude in said plurality of pulses a reference level corresponding to the average peak level thereof, means for detecting those of said pulses in said train having amplitudes which are approximately of amplitudes which are certain percentages of said reference level, and means for providing outputs representing said information from those of said electrical signals which are substantially coincidental with said pulses.

41. The invention as set forth in claim 40 wherein said detecting means includes means for detecting first and second pulses which respectively precede and succeed at least one of said pulses of highest amplitude.

42. The invention as set forth in claim 41 wherein said first and second pulses detecting means includes means for detecting, as said first pulse and second pulses, pulses having amplitudes which are different percentages of said reference level.

43. The invention as set forth in claim 42 wherein first and second pulse detecting means include (a) means for detecting said first pulse when said first pulse is a member of a first set of at least three adjacent pulses in said train one of which is of amplitude equal to or greater than a first of said different percentage of said reference level and the others of which are of amplitudes less than said first percentage of said reference level, said first pulse being the one of said pulses in said pair of amplitude equal to or greater than said first percentage of said reference level and which is closest to said one pulse of highest amplitude, and (b) means for detecting said second pulse when said second pulse is a member of a second set of at least three adjacent pulses in said train one of which is of amplitude equal to or greater than a second of said different percentages of said reference level and the others of which are of amplitude less than said second percentage of said reference level, said second pulse being the member of said second pair of amplitude equal to or greater than said second percentage of said reference level and which is closest to said one pulse of highest amplitude level.

44. The invention as set forth in claim 43 wherein said information is systolic and diastolic blood pressure and said detecting means includes means for establishing said first percentage as about 45% and said second percentage as about 75%, whereby said outputs providing means provides the one of said outputs which is coincident with said first pulse as representing said systolic pressure and the other of said outputs which is coincident with said second pulse as representing said diastolic pressure.

45. The invention as set forth in claim 44 further comprising means for timing the duration of the total time between a plurality of pairs of said pulses which occur sequentially in said train, and means for deriving another output representing pulse rate from the said duration of said sequentially occurring pulses.

46. The invention as set forth in claim 43 wherein said deriving means includes means for selecting a set of pulses of highest amplitude, the highest amplitude one of which is at most 25% higher than the amplitude of the lowest pulses in said set and said highest amplitude one of said pulses is no more than 150% of both of a pair of pulses which are consecutive therewith and are next adjacent thereto.

47. The invention as set forth in claim 46 including means for detecting an error in said information when less than a certain number of pulses occur in said train.

48. The invention as set forth in claim 47 wherein said error detecting means also includes means for detecting an error when said first pulse is the first pulse in said train.

49. The invention as set forth in claim 48 wherein said error detecting means also includes means for detecting an error when less than a certain number of pulses occur in said train after said second pulse.

50. Apparatus for obtaining information as to the vascular condition of a body comprising
    means for producing a change in circulation through a blood vessel and generating electrical signals corresponding thereto,
    means for translating said signals into a train of pulses which correspond to the pressure pulsations in said blood vessel as said circulation changes,
    means for selecting certain pulses in said train which comprises an envelope detector for providing an output signal which follows the peaks of the pulses in said train, a peak detector which provides an output signal having an amplitude corresponding to the peak amplitude of that envelope detector output signal, multiplier means for providing a systolic threshold level which is a certain percentage of said peak detector signal level and a diastolic threshold level which is another percentage of said peak detector output level, comparators for outputting trigger signals when said envelope reaches said systolic reference level and said diastolic threshold level, respectively, and
    means for providing outputs representing said information includes means operated by said trigger signals for producing as said outputs, signals corresponding to the amplitude of said electrical signals which correspond to the circulation through said blood vessel upon occurrence of said systolic trigger signal and upon occurrence of said diastolic trigger signal, the amplitude of said electrical signals produced upon occurrence of said systolic trigger signal being a measure of the systolic blood pressure in said vessel and the amplitude of said electrical signal produced upon occurrence of said diastolic trigger being a measure of the diastolic blood pressure in said blood vessel.

51. Apparatus for obtaining information as to blood pressure comprising
    means for providing electrical signals corresponding to the constriction pressure exerted on a blood vessel as the constriction thereof is changed,
    means for translating said electrical signals into a train of successive pulses each corresponding to a successive pulsation of said vessel and having an amplitude which is a function of the pulsatile component of the blood pressure,
    means for translating said electrical signals into first digital signals each corresponding to a different one of said pulses in said train and representing the amplitude of said electrical signals when each of said pulses in said train occur, which first digital signals represent the constriction pressure on said vessel,
    means for storing all said first digital signals,
    means for storing all second digital signals representing the amplitudes of said pulses in said train,
    means for developing from said pulses in said train a reference level corresponding to the average of the amplitudes of a set of those of said pulses in said train which are of highest amplitude level regardless of where they occur in said train,
    means for identifying from said stored second digital signals first and second pulses in said train respectively having amplitudes at least equal to a systolic threshold level and a diastolic threshold level each of which are different percentages of said reference level, and
    means for displaying as said systolic blood pressure and as said diastolic blood pressure the values of said first digital signals respectively corresponding to said first pulse and to said second pulse.

52. The invention as set forth in claim 51 wherein said developing means includes
    (i) means for storing a peak table of third digital signals which correspond to those pulses in said train which are of highest amplitude, said third digital signals each representing the amplitude of a different one of said highest amplitude pulses,
    (ii) means for selecting those of said third digital signals which correspond to three pulses in said train and have amplitudes, the highest of which is at most a first predetermined percentage of the smallest and the highest of which is at most a second predetermined percentage of the amplitudes of each of the pair of pulses next adjacent thereto in said train, said three pulses constituting said set, and
    (iii) means for obtaining from said third digital signals corresponding to the pulses in said set, a digital signal representing said reference level.

53. The invention as set forth in claim 52 wherein said identifying means includes means for selecting said first and second pulses from said stored second digital signals located on opposite sides of the one of said second digital signals which corresponds to said highest amplitude pulse, said vessel being in a more constricted condition while the pulses on the one of said opposite sides which includes said first pulse are being produced than while the pulses on the other of said opposite sides which include said second pulse are being produced, and said first and second pulses being members of different sets of at least three pulses which correspond to digital signals of values one of which is at least equal to said threshold values and the other two of which are both less than said threshold values, said one pulse of said set being closest to said highest amplitude pulses and said first and second pulses being said one pulses of their respective sets.

54. The invention as set forth in claim 53 including means for measuring the intervals of time between the pulses of each pair of pulses in said train, and means for inhibiting said means for displaying said pressures if more than a predetermined number of said intervals are greater than a given length.

55. The invention as set forth in claim 54 including means for inhibiting said means for displaying said systolic pressure if said first pulse corresponds to the one of said second digital signals which is located at an end of said table.

56. The invention as set forth in claim 55 including means for also inhibiting said means for displaying said pressures if less than a certain number of second digital signals are stored.

57. The invention as set forth in claim 56 including further means for inhibiting said means for displaying said pressures unless the values of the one of the first digital signals corresponding to said first pulse is at least the sum of the value of said first digital signal corresponding to said second pulse and a value corresponding to a certain pressure which is lower than any normal blood pressure difference between systolic and diastolic pressures.

58. The invention as set forth in claim 52 including cuff means for changing the constriction of said vessel which applies pressure externally to the body member which carries said blood vessel and which releases said pressure; and said means for providing said electrical signals includes means for transducing the pressure at said cuff means into said electrical signals as said cuff means pressure changes in one of two opposite senses, in the first of which said pressure is applied and in the second of which said pressure is released; and wherein said means for storing said second digital signals is operative to establish a pulse table of said second digital signals representing the heights of said pulses as said cuff means pressure changes in said one sense from a first cuff pressure to a second cuff pressure; and said means for storing said first digital signals is operative to establish a cuff table of said first digital signals representing the static pressure presented by said cuff means when each of said pulses occur as said cuff means pressure changes from said first cuff pressure to said second cuff pressure, and said means for storing said first and second digital signals in said pulse table and in said cuff table are operative to store said first and second digital signals in said tables until certain digital signals in said tables satisfy predetermined criteria.

59. The invention as set forth in claim 58 wherein said storing means includes means responsive to said first and second digital signals for storing said signals in said cuff table and pulse table until said criteria which are met are that (a) at least a certain number of said second digital signals are stored in said pulse table after the storage of the one of said second digital signals which corresponds to a pulse near the middle of said peak table between approximately like numbers of digital signals corresponding to pulses of higher amplitude and of lower amplitude which are also stored in said peak table, (b) the one of said first digital signals in said cuff table which represents the last cuff pressure in said cuff table has a value which is predetermined by the value of the third digital signal representing the lowest one of the pulses in said peak table, and (c) there are at least two consecutive second digital signals stored in said pulse table after the storage of said one of said second digital signals which corresponds to said pulse near the middle of said peak table which represents values below a predetermined threshold value corresponding to a predetermined percentage of the average of the three lowest third digital signals in said peak table.

60. The invention as set forth in claim 59 wherein means included in said storing means includes means for storing said first and second digital signals in said cuff table and said pulse table nevertheless until said tables are fully occupied if any of said criteria remain unsatisfied.

61. The invention as set forth in claim 60 including means for developing said systolic threshold value which is 0.45 times the said average from the amplitude of said set of three highest third digital signals in said peak table and for developing said diastolic threshold which is 0.75 times said last named average.

62. The invention as set forth in claim 60 including means for obtaining information respecting pulse rate operative first to measure the time interval for the occurrence of a group of said pulses the first of which occurs after the occurrence of a plurality of pulses commencing with the pulse following the pulse which corresponds to the digital signal in said peak table having the lowest amplitude, and means for obtaining said pulse rate information in terms of the average rate at which the pulses in said group occurs.

63. The invention as set forth in claim 60 wherein said identifying means includes (a) means for obtaining from said reference level said diastolic threshold level in terms of the product of average level of the pulses in said set and a factor which is about 0.75, (b) means for obtaining from said reference level said systolic threshold in terms of the product of said average level of the pulses in said set and a factor which is about 0.45, (c) means for selecting a set of said second digital signals in said pulse table from those second digital signals therein which correspond to three consecutive pulses more than two pulses beyond the pulse which is located in the middle of said peak table on the side of said middle pulse in the direction of lower cuff pressures, which said set of second digital signals represent two values below said diastolic threshold level and one value at least equal to said diastolic threshold level said digital signal having a said one value corresponding to said second pulse, and (d) means for selecting another set of second digital signals in said pulse table from those second digital signals which correspond to three consecutive pulses more than two pulses beyond the pulse which is located in the middle of said peak table in the direction of higher cuff pressures, which said another set of second digital signals represent two values below and one value at least equal to said systolic threshold level, said digital signal having said one value corresponding to said first pulse.

64. The method of measuring blood pressure by the use of the arterial pressure pulses of varying amplitude which accompany the temporary constriction of an artery by means of a compression cuff or the like, said method comprising translating said pulses into corresponding electrical signals, storing digital signals corresponding to the amplitudes of said electrical signals, deriving from said stored digital signals a reference level related to at least one of said digital signals which corresponds to a pressure pulse of highest amplitude and a predetermined threshold level which is less than said reference level, selecting a plurality of said stored signals corresponding to a plurality of successive ones of said pulses the amplitudes of which and said threshold bear a predetermined relationship with each other, and then providing an output corresponding to the pressure exerted by the blood in said artery upon occurrence of a selected one of said plurality of successive ones of said pulses.

65. A system for measuring blood pressure by the use of the arterial pressure pulses of varying amplitude which accompany the temporary constriction of an artery by means of a compression cuff or the like, said system comprising means for translating said pulses into corresponding electrical signals, means for storing digital signals corresponding to the amplitudes of said electrical signals, means for deriving from said stored digital signals a reference level related to at least one of said digital signals corresponding to a pressure pulse of highest amplitude and the predetermined threshold level which is less than said reference level, means for selecting a plurality of said stored signals corresponding to a plurality of successive ones of said pulses, the amplitudes of which and said threshold level bear a predetermined relationship, and means for providing an output corresponding to the pressure exerted by the blood in said artery upon occurrence of a selected one of said successive ones of said plurality of pulses.

* * * * *